US012605379B2

(12) United States Patent
de los Rios et al.

(10) Patent No.: US 12,605,379 B2
(45) Date of Patent: *Apr. 21, 2026

(54) METHODS OF IMPROVING LUNG FUNCTION

(71) Applicant: Endeavor BioMedicines, Inc., San Diego, CA (US)

(72) Inventors: Miguel de los Rios, San Diego, CA (US); John Hood, Del Mar, CA (US); Anita J. DiFrancesco, San Diego, CA (US); Luis A. Dellamary, San Marcos, CA (US); Paul A. Frohna, Solana Beach, CA (US)

(73) Assignee: Endeavor BioMedicines, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/327,682

(22) Filed: Sep. 12, 2025

(65) Prior Publication Data

US 2026/0007663 A1 Jan. 8, 2026

Related U.S. Application Data

(63) Continuation of application No. 19/070,439, filed on Mar. 4, 2025, now Pat. No. 12,447,148.

(60) Provisional application No. 63/711,648, filed on Oct. 24, 2024, provisional application No. 63/649,067, filed on May 17, 2024, provisional application No. 63/561,444, filed on Mar. 5, 2024.

(51) Int. Cl.
*A61K 31/502* (2006.01)
*A61P 11/00* (2006.01)

(52) U.S. Cl.
CPC ............ *A61K 31/502* (2013.01); *A61P 11/00* (2018.01)

(58) Field of Classification Search
CPC .............................. A61K 31/502; A61P 11/00
USPC .......................................................... 514/248
See application file for complete search history.

(56) References Cited

U.S. PATENT DOCUMENTS

| | | | |
|---|---|---|---|
| 4,289,772 | A | 9/1981 | Campbell et al. |
| 7,981,892 | B2 | 7/2011 | Hipskind et al. |
| 8,273,742 | B2 | 9/2012 | Hipskind et al. |
| 9,000,023 | B2 | 4/2015 | Hipskind et al. |
| 11,154,541 | B2 | 10/2021 | Xie |
| 11,628,167 | B2 | 4/2023 | de los Rios et al. |
| 12,213,974 | B2 | 2/2025 | de los Rios et al. |
| 12,295,954 | B2 | 5/2025 | de los Rios et al. |
| 12,447,148 | B2 * | 10/2025 | de los Rios ............. A61P 11/00 |
| 2010/0324048 | A1 | 12/2010 | Hipskind et al. |
| 2011/0183948 | A1 | 7/2011 | Levine et al. |
| 2011/0301162 | A1 | 12/2011 | Deak et al. |
| 2016/0341726 | A1 | 11/2016 | Humphreys et al. |
| 2018/0256570 | A1 | 9/2018 | Peterson et al. |
| 2019/0255042 | A1 | 8/2019 | Cai et al. |
| 2020/0000784 | A1 | 1/2020 | Xie |
| 2021/0315871 | A1 | 10/2021 | Xie |
| 2022/0265650 | A1 * | 8/2022 | de los Rios ............. A61P 11/00 |
| 2022/0354832 | A1 | 11/2022 | Xie |
| 2023/0201195 | A1 | 6/2023 | de los Rios et al. |
| 2023/0201196 | A1 | 6/2023 | de los Rios et al. |
| 2024/0342170 | A1 | 10/2024 | de los Rios et al. |
| 2025/0235452 | A1 | 7/2025 | de los Rios et al. |
| 2025/0281484 | A1 | 9/2025 | de los Rios et al. |
| 2026/0007664 | A1 | 1/2026 | de los Rios et al. |

FOREIGN PATENT DOCUMENTS

| | | | |
|---|---|---|---|
| GB | 2528298 | A | 1/2016 |
| JP | 2012-530705 | A | 12/2012 |
| WO | WO-9726258 | A1 | 7/1997 |
| WO | WO-99/52534 | A1 | 10/1999 |
| WO | WO-00/74706 | A1 | 12/2000 |
| WO | WO-2003/088970 | A2 | 10/2003 |
| WO | WO-04/020599 | A2 | 3/2004 |
| WO | WO-2005/033288 | A2 | 4/2005 |
| WO | WO-2005/080378 | A1 | 9/2005 |
| WO | WO-2006/004589 | A2 | 1/2006 |
| WO | WO-2006/028958 | A2 | 3/2006 |
| WO | WO-2008/028689 | A1 | 3/2008 |
| WO | WO-2008/110611 | A1 | 9/2008 |
| WO | WO-2009/002469 | A1 | 12/2008 |
| WO | WO-2009/035568 | A1 | 3/2009 |
| WO | WO-2009/134574 | A2 | 11/2009 |
| WO | WO-2010/007120 | A1 | 1/2010 |
| WO | WO-2010/056588 | A1 | 5/2010 |
| WO | WO-2010/056620 | A1 | 5/2010 |
| WO | WO-2010/062507 | A1 | 6/2010 |
| WO | WO-2010/147917 | A1 | 12/2010 |
| WO | WO-2014/191736 | A1 | 12/2014 |
| WO | WO-2017/095757 | A1 | 6/2017 |
| WO | WO-2020/018904 | A1 | 1/2020 |

(Continued)

OTHER PUBLICATIONS

Maher et al.. ENV-101, A Novel Hedgehog Inhibitor, Increases Lung Function, and Reduces Lung Fibrosis in Patients With Idiopathic Pulmonary Fibrosis: InA18. Fixing What's Broken: Novel Therapeutics for Lung Remodeling May 2024 (pp. A1056-A1056). American Thoracic Society. (Year: 2024).*

(Continued)

*Primary Examiner* — Yih-Horng Shiao
(74) *Attorney, Agent, or Firm* — Choate, Hall & Stewart LLP; Kristen C. Buteau; William C. Howland, III

(57) ABSTRACT

The present disclosure provides methods of treating pulmonary fibrosis, the methods comprising administering taladegib to a subject in need thereof.

29 Claims, 11 Drawing Sheets

(56) References Cited

FOREIGN PATENT DOCUMENTS

| | | | |
|---|---|---|---|
| WO | WO-2022/081661 A1 | | 4/2022 |
| WO | WO-2024/182483 A1 | | 9/2024 |
| WO | WO-2025/188802 A1 | | 9/2025 |

OTHER PUBLICATIONS

Aribindi, K. et al. Emerging pharmacological options in the treatment of idiopathic pulmonary fibrosis (IPF), Expert Review of Clinical Pharmacology, 17(9):817-835 (2024).

Author Unknown, Glossary of Medical Education Terms (Revised Feb. 2002). Institute for International Medical Education (IIME), 22 pages. Retrieved from the internet <<https:// www.iime.org/glossary.htm>> on Apr. 20, 2024.

Bendell, J. et al., A Phase I Dose-Escalation, Pharmacokinetic (PK) and Pharmacodynamic (PD) Evaluation of LY2940680, an Oral Smoothened (Smo) Inhibitor/Poster, 24th European Cancer Organization (ECCO) EORTC-NCI-AACR Symposium on Molecular Targets and Cancer Therapeutics. Dublin, Ireland, 2012.

Bendell, J. et al., Phase I Study of LY2940680, a Smo Antagonist, in Patients with Advanced Cancer Including Treatment-Naive and Previously Treated Basal Cell Carcinoma, Clinical Cancer Research, 24(9):2082-2091 (2019).

Bender, M. et al., Abstract 2819: Identification and Characterization of a Novel Smoothened Antagonist for the Treatment of Cancer with Deregulated Hedgehog Signaling. Presented at the AACR 102nd Annual Meeting. Orlando, FL, 2011.

Bhowmick, N. et al., TGF-beta signaling in fibroblasts modulates the oncogenic potential of adjacen epithelia, Science, 303(5659):848-851 (2004).

Bonow, R. et al., Population-wide trends in aortic stenosis incidence and outcomes, Circulation, 131 (11):969-971 (2015).

Boudoulas, K. et al., Etiology of valvular heart disease in the 21st century, Cardiology, 126:139-152 (2013).

Casaclang-Verzosa, G. et al., Echocardiographic Approaches and Protocols for Comprehensive Phenotypic Characterization of Valvular Heart Disease in Mice, J Vis Exp., 14(120):54110 (2017).

Chu, Y. et al., Fibrolic Aortic Valve Stenosis in Hypercholesterolemic/Hypertensive Mice, Arterioscler Thromb Vase Biol., 36(3):466-474 (2016).

Clinical Trials ID: NCT04968574, A Study Evaluating the Safety and Efficacy of ENV-101 in Subjects With Idiopathic Pulmonary Fibrosis (IPF), Version 11, Posted Feb. 21, 2024, 8 pages, < https://clinicaltrials.gov/study/NCT04968574?intr=env-101&rank=4&tab=history&a=11#version-content-panel>.

Clinical Trials ID: NCT04968574, A Study Evaluating the Safety and Efficacy of ENV-101 in Subjects With Idiopathic Pulmonary Fibrosis (IPF), Version 12, Posted Feb. 21, 2024, 8 pages, < https://clinicaltrials.gov/study/NCT04968574?intr=env-101&rank=4&tab=history&a=12#version-content-panel>.

Clinical Trials ID: NCT05199584, A Study Evaluating the Safety and Efficacy of ENV-101 (Taladegib) in Patients With Advanced Solid Tumors Harboring PTCH1 Loss of Function Mutations Fibrosis (IPF), Version 16, Posted Dec. 14, 2023, 7 pages, < https://clinicaltrials.gov/study/NCT05199584?intr=env101&rank=1&tab=history&a=16#version-content-panel >.

Clinical Trials ID: NCT05817240, A Drug-Drug Interaction Study of ENV-101 (Taladegib) on Nintedanib Pharmacokinetics in Healthy Subjects, Version 4, Posted Dec. 14, 2023, 5 pages, < https://clinicaltrials.gov/study/NCT05817240?intr=env-101&rank=3&tab=history&a=4#version-content-panel>.

Clinical Trials ID: NCT06422884, A Phase 2 Trial of ENV-101 in Patients With Lung Fibrosis (WHISTLE-PF Trial), Version 1, Posted May 15, 2024, 12 pages, < https://clinicaltrials.gov/study/NCT06422884?intr=env-101&rank=2&tab=history&a=1#version-content-panel>.

Clinical Trials ID: NCT06422884, A Phase 2 Trial of ENV-101 in Patients With Lung Fibrosis (WHISTLE-PF Trial), Version 2, Posted Nov. 21, 2024, 12 pages, < https://clinicaltrials.gov/study/NCT06422884?intr=env-101&rank=2&tab=history&a=2#version-content-panel>.

Clinical Trials ID: NCT06422884, A Phase 2 Trial of ENV-101 in Patients With Lung Fibrosis (WHISTLE-PF Trial), Version 3, Posted Dec. 8, 2024, 16 pages, < https://clinicaltrials.gov/study/NCT06422884?intr=env-101&rank=2&tab=history&a=3#version-content-panel>.

Clinical Trials ID: NCT06422884, A Phase 2 Trial of ENV-101 in Patients With Lung Fibrosis (WHISTLE-PF Trial), Version 4, Posted Jan. 21, 2025, 16 pages, < https://clinicaltrials.gov/study/NCT06422884?intr=env-101&rank=2&tab=history&a=4#version-content-panel>.

Coffey, S. et al., The prevalence, incidence, progression, and risks of aortic valve sclerosis: a systematic review and meta-analysis, J Am Coll Cardiol, 63(25 Pt A):2852-2861 (2014).

Damen, FW. et al., High-Frequency 4-Dimensional Ultrasound (4DUS): A Reliable Method for Assessing Murine Cardiac Function, Tomography, 3(4):180-187 (2017).

Dummer, R. et al., The 12-month analysis from Basal Cell Carcinoma Outcomes with LDE225 Treatment (BOLT): A phase 11, randomized, double-blind study of sonidegib in patients with advanced basal cell 15 carcinoma, J Am Acad Dermatol., 75(1):113-125 e115 (2016).

Dweck, M. R. et al, Calcific aortic stenosis: a disease of the valve and the myocardium, Journal of the American College of Cardiology., 60(19): 1854-1863 (2012).

Edeling, M. et al., Developmental signalling pathways in renal fibrosis: the roles of Notch, Wnt and Hedgehog, Nav Rev Nephrol., 12(7):426-439 (2016).

Espinosa-Bustos et al., State of the art of Smo antagonists for cancer therapy: advances in the target receptor and new ligand structures, Future Med. Chem., 11(6): 615-636 (2019).

Faggiano, P. et al., Epidemiology and cardiovascular risk factors of aortic stenosis, Cardiovasc Ultrasound, 4:27 (2006).

Frank-Kamenetsky, M., et al., Small-molecular modulators of Hedgehog signaling: identification and characterization of Smoothened agonists and antagonists, Journal of Biolology 1(2):1-10 (2002).

Gao, Z. et al., Effect of mutations on drug resistance of smoothened receptor toward inhibitors probed by molecular modeling, Elsevier, 741 (2020).

Goldin, J. et al., Longitudinal Changes in Quantitative Interstitial Lung Disease on Computed Tomography after Immunosuppression in the Scleroderma Lung Study II, Annals of the American Thoracic Society, 15(11):1286-1295 (2018).

Hirsova, P. et al., Vismodegib suppresses TRAIL-mediated liver injury in a mouse model of nonalcoholic steatohepatitis, PLOS One, 8(7): e70599 (2013).

Horn, A., et al., Inhibition of hedgehog signalling prevents experimental fibrosis and induces regression of established fibrosis, Ann Rheum Dis., 71(5):785-9 (2012).

Hu, B. et al., Reemergence of hedgehog mediates epithelial-mesenchymal crosstalk in pulmonary fibrosis, Am J Respir Cell Mol Biol, 52(4): 418-28 (2015).

Hu, L. et al., An overview of hedgehog signaling in fibrosis, Mol Pharmacol, 87(2): 174-82 (2015).

International Search Report and Written Opinion mailed Mar. 24, 2022 for International Application Serial No. PCT/US2021/054713 filed on Oct. 13, 2021.

International Search Report for PCT/US2010/038568, 4 pages (mailed Jul. 28, 2010).

International Search Report for PCT/US24/17611, 2 pages (mailed Jun. 5, 2024).

International Search Report for PCT/US25/18407, 6 pages (mailed Jun. 17, 2025).

Jacob, J. et al., Mortality prediction in idiopathic pulmonary fibrosis: evaluation of computer-based CT analysis with conventional severity measures, European Respiratory Journal, 49(1):1601011 (2017).

Jacobsen, A. et al., Hedgehog Pathway Inhibitor Therapy for Locally Advanced and Metastatic Basal Cell Carcinoma: A Systematic Review and Pooled Analysis of Interventional Studies, JAMA Dermatol., 152(7):816-824 (2016).

(56) References Cited

OTHER PUBLICATIONS

Jia, Y., The Hedgehog pathway: role in cell differentiation, polarity and proliferation, Arch Toxicol., 89(2):179-191 (2015).
Kim, H. et al., Quantitative texture-based assessment of one-year changes in fibrotic reticular patterns on HRCT in scleroderma lung disease treated with oral cyclophosphamide, 12:2455-2465 (2011).
Kim, H. et al., Transitions to different patterns of interstitial lung disease in scleroderma with and without treatment, Clinical and Epidemiological Research, 75(7):1367-1371 (2016).
Lam, CW et al., A frequent activated smoothened mutation in sporadic basal cell carcinomas, Oncogene, 18(3):833-836 (1999).
Lear, J. T., Oral hedgehog-pathway inhibitors for basal-cell carcinoma, N Engl J Med, 366(23):2225-6 (2012).
Lee, J., et al., A small-molecule antagonist of the Hedgehog signaling pathway, ChemBioChem, 8(2016):1916-1919 (2007).
Lomanta, J. et al., Pulmonary Function and Chest Computed Tomography (CT) Scan Findings After Antifibrotic Treatment for COVID-19-Related Pulmonary Fibrosis, Am J Case Rep., 23: e934830 (2022).
Maher, T. M. et al., ENV-101, a Novel Hedgehog Inhibitor, Increases Lung Function and Reduces Lung Fibrosis in Patients with Idiopathic Pulmonary Fibrosis: Results from a m Randomized, Double-blind, Placebo-controlled Phase 2 Trial, oral presentation at ATS 2024, San Diego, CA on May 19, 2024.
Maher, T. M. et al., ENV-101, a Novel Hedgehog Inhibitor, Increases Lung Function and Reduces Lung Fibrosis in Patients with Idiopathic Pulmonary Fibrosis: Results from a Randomized, Double-blind, Placebo-controlled Phase 2 Trial, presented at ATS 2024, San Diego, CA on May 19, 2024.
Maher, T. M. et al., ENV-101, A Novel Hedgehog Inhibitor, Increases Lung Function, and Reduces Lung Fibrosis in Patients With Idiopathic Pulmonary Fibrosis: Results From a Randomized, Double-blind, Placebo-controlled Phase 2 Trial, Am J. Respir Crit., 209:A1056 (2024).
Mao, J. et al., A novel somatic mouse model to survey tumorigenic potential applied to the Hedgehog pathway, Cancer Res., 66(20):10171-10178 (2006).
McMahon, G., VEGF Receptor Signaling in Tumor Angiogenisis, The Oncologist, 5(suppl 1):3-10 (2000).
Moshai, E. et al., Targeting the hedgehog-glioma-associated oncogene homolog pathway inhibits bleomycin-induced lung fibrosis in mice, Am J Respir Cell Mol Bio., 51(1): 11-25 (2014).
Noble, P. W. et al., Pulmonary fibrosis: patterns and perpetrators, Journal of Clinical Investigation. 122(8): 2756-2762) (2012).
Paudel, A. et al., Manufacturing of solid dispersions of poorly water soluble drugs by spray drying: formulation and process considerations, Int. J. Pharm., 453(1): 253-284 (2013).
Pinedo, et al., Translational Research: The Role of VEGF in Tumor Angiogenesis, The Oncologist, 5(suppl 1):1-2 (2000).
Rudin, C. et al., Treatment of Medulloblastoma with Hedgehog Pathway Inhibitor GDC-0449, N Engl. J Med., 361:12 (2009).
Sekulic, A. et al., Efficacy and Safety of Vismodegib in Advanced Basal-Cell Carcinoma, N. Engl. J. Med., 366(23): 2171-2179 (2012).
Sekulic, A. et al., Long-term safety and efficacy of vismodegib in patients with advanced basal cell carcinoma: final update of the pivotal Erivance BCC study, BMC Cancer, 17(1):332 (2017).
Stewart, G. et al., Expression of the developmental Sonic hedgehog (Shh) signalling pathway is up-regulated in chronic lung fibrosis and the Shh receptor patched 1 is present in circulating T lymphocytes, J Pathol., 199:488-495 (2003).
Tremblay, M., et al., Recent patents for Hedgehog pathway inhibitors for the treatment of malignancy, Expert Opin. Ther. Patents, 19(8):1039-1056 (2009).
Tremblay, M., et al., Semisynthetic cyclopamine analogues as potent and orally bioavailable Hedgehog pathway antagonists, J. Med. Chem., 51: 6646-6649 (2008).
Ueno, H. et al., A phase I and pharmacokinetic study of taladegib, a Smoothened inhibitor, in Japanese patients with advanced solid tumors, Investigational New Drugs, 1-10 (2017).
Wang, C. et al., Synthesis and evaluation of novel dimethylpyridazine derivatives as hedgehog signaling pathway inhibitors, Bioorganic & Medicinal Chemistry, 26(12): 3308-3320 (2018).
Wang, C. et al., Synthesis and evaluation of novel dimethylpyridazine derivatives as hedgehog signaling pathway Inhibitors, CASREACT 169:165515, 4 pages (2018).
Wikipedia, HEK 293 cells, http://en.wikipedia.org/wiki/HEK_293_cells, last modified on Jun. 3, 2014 and downloaded on Jul. 15, 2014.
Wilson, M. S. et al., Pulmonary fibrosis: pathogenesis, etiology and regulation, Mucosal Immunology, 2(2): 103-121 (2009).
Written Opinion for PCT/US2010/038568, 5 pages (mailed Jul. 28, 2010).
Written Opinion for PCT/US24/17611, 5 pages (mailed Jun. 5, 2024).
Written Opinion for PCT/US25/18407, 12 pages (mailed Jun. 17, 2025).
Xie, J. et al., Activating Smoothened mutations in sporadic basal-cell carcinoma, Nature, 391 (6662):90-92 (1998).
Yang, L. et al., Identification of signature genes for detecting hedgehog pathway activation in esophageal cancer, Pathol. Oncol. Res., 17:387-391 (2011).
Zhu et al., L-4, a Well-Tolerated and Orally Active Inhibitor of Hedgehog Pathway, Exhibited Potent Anti-Tumor Effects Against Medulloblastoma in vitro and in vivo, Frontiers in Pharmacology, 10(89):1-13 (2019).
Sato, Y. et al., Blockade of Hedgehog Signaling Attenuates Biliary Cystogenesis in the Polycystic Kidney (PCK) Rat, Am. J. Pathol., 188(10):2251-2263 (2018).
Zhou, D. et al., Sonic hedgehog signaling in kidney fibrosis: a master communicator, Sci. China Life Sci., 59(9):920-929 (2016).

* cited by examiner

METHODS OF IMPROVING LUNG FUNCTION

BACKGROUND

Interstitial lung diseases (ILDs) are a group of more than 200 fibrotic disorders that cause scarring in the lungs, damaging tissues in or around the lungs' alveoli.

Idiopathic pulmonary fibrosis (IPF) and non-IPF progressive pulmonary fibrosis (PPF) are ILDs with a terminal prognosis. IPF is the most common ILD, and its origin is unknown. PPF is a subset of non-IPF fibrosing ILDs with a progressive course of disease despite conventional treatment. In the United States alone, the prevalence of IPF is estimated to be about 150,000 subjects, with an estimated 20,000 to 40,000 individuals diagnosed annually. The prevalence of PPF is about 186,000 in the United States, with an estimated 84,000 individuals diagnosed annually. The current standards of care for IPF and PPF modestly slow the decline of lung function and do not reverse the course of disease.

SUMMARY

The understanding of IPF has progressed greatly over the past decade with a clear understanding that the driver of the disease is a dysregulated tissue remodeling rather than inflammation. IPF is now understood to be a chronic wound with characteristics identical to a wound healing process except that it is excessive and unrelenting. Wound healing processes are driven by fibroblast activation and trans differentiation of cells into myofibroblasts which deposit fibrotic extracellular matrix and contract tissue. The dominant pathway that governs fibroblast activation and myofibroblast accumulation is the Hedgehog (Hh) pathway through activation of Smoothened (Smo).

Myofibroblasts are key cellular drivers for IPF. The initial step in IPF is injury of lung alveolar epithelial cells via environmental toxins or viral infection. Patients present with IPF long after the initial injury, so this causative step involving inflammation is generally unknown and inflammation is less relevant by the time of presentation. As part of the wound healing process after initial insult, Sonic Hedgehog (SHh) is secreted. SHh activates fibroblasts and initiates epithelial mesenchymal transition (EMT) leading to production and activation of myofibroblasts in a Smo-dependent manner. Myofibroblasts secrete collagen and other extracellular matrix (ECM) proteins by which they adhere to and contract tissue, ultimately pulling the lung closed (i.e., reducing lung elasticity, capacity and function) like a wound. The action of myofibroblasts is the primary cause of IPF pathology and therefore inhibition of the Hh pathway uniquely targets the driver of IPF disease.

Myofibroblasts are derived via EMT mediated by Hedgehog or transforming growth factor (TGF) in a Hedgehog-dependent fashion. Both SHh and TGF drive differentiation of fibroblasts and other cells into myofibroblasts in a process governed by Smo. This positive feedback loop becomes dysregulated in IPF resulting in accumulation of myofibroblasts. Increased production of intracellular alpha-smooth muscle actin (αSMA) is a key characteristic of differentiated myofibroblasts and IPF fibrotic foci are rife with αSMA. Inhibition of Hedgehog results in apoptosis or deactivation of myofibroblasts. SHh and activation of the Hh pathway protect myofibroblasts from apoptosis, resulting in accumulation of the cellular driver of IPF. Disruption of the Hh pathway reduces the myofibroblast production of ECM such as collagen and intracellular αSMA, both of which are required for contraction. Additionally, inhibition of Smo re-sensitizes myofibroblasts to apoptotic processes.

In some embodiments, the present disclosure provides the unexpected and surprising insight that the Hedgehog inhibitor taladegib is a disease-modifying agent in fibrotic diseases. Indeed, the present disclosure encompasses the recognition that taladegib causes apoptosis of myofibroblasts, thereby eliminating the driver of pulmonary fibrotic pathology. Accordingly, in some embodiments, the present disclosure provides a method of inducing apoptosis of myofibroblasts in a subject in need thereof, the method comprising administering taladegib, or a pharmaceutically acceptable salt thereof, to the subject. In some such embodiments, the method comprises administering a therapeutically effective amount of taladegib, or a pharmaceutically acceptable salt thereof. In some such embodiments, a therapeutically effective amount of taladegib, or a pharmaceutically acceptable salt thereof, is about 10-200 mg. In some such embodiments, a therapeutically effective amount of taladegib, or a pharmaceutically acceptable salt thereof, is about 100-200 mg. In certain embodiments, the therapeutically effective amount of taladegib, or a pharmaceutically acceptable salt thereof, is about 100 mg. In some embodiments, the therapeutically effective amount of taladegib, or a pharmaceutically acceptable salt thereof, is about 100 mg administered once a day. In certain embodiments, the therapeutically effective amount of taladegib, or a pharmaceutically acceptable salt thereof, is about 150 mg. In some embodiments, the therapeutically effective amount of taladegib, or a pharmaceutically acceptable salt thereof, is about 150 mg administered once a day. In certain embodiments, the therapeutically effective amount of taladegib, or a pharmaceutically acceptable salt thereof, is about 200 mg. In some embodiments, the therapeutically effective amount of taladegib, or a pharmaceutically acceptable salt thereof, is about 200 mg administered once a day.

In some embodiments, the present disclosure provides a method of treating pulmonary fibrosis, the method comprising administering taladegib, or a pharmaceutically acceptable salt thereof, to a subject in need thereof. In some such embodiments, the method comprises administering a therapeutically effective amount of taladegib, or a pharmaceutically acceptable salt thereof. In some such embodiments, a therapeutically effective amount of taladegib, or a pharmaceutically acceptable salt thereof, is about 10-200 mg. In some such embodiments, a therapeutically effective amount of taladegib, or a pharmaceutically acceptable salt thereof, is about 100-200 mg. In certain embodiments, the therapeutically effective amount of taladegib, or a pharmaceutically acceptable salt thereof, is about 100 mg. In some embodiments, the therapeutically effective amount of taladegib, or a pharmaceutically acceptable salt thereof, is about 100 mg administered once a day. In certain embodiments, the therapeutically effective amount of taladegib, or a pharmaceutically acceptable salt thereof, is about 150 mg. In some embodiments, the therapeutically effective amount of taladegib, or a pharmaceutically acceptable salt thereof, is about 150 mg administered once a day. In certain embodiments, the therapeutically effective amount of taladegib, or a pharmaceutically acceptable salt thereof, is about 200 mg. In some embodiments, the therapeutically effective amount of taladegib, or a pharmaceutically acceptable salt thereof, is about 200 mg administered once a day.

In some embodiments, the present disclosure provides a method of improving lung function in a subject suffering from or diagnosed with pulmonary fibrosis, for example, idiopathic pulmonary fibrosis (IPF) or non-IPF progressive pulmonary fibrosis (PPF), the method comprising administering taladegib, or a pharmaceutically acceptable salt thereof, to the subject. In some such embodiments, the method comprises administering a therapeutically effective amount of taladegib, or a pharmaceutically acceptable salt thereof. In some such embodiments, a therapeutically effective amount of taladegib, or a pharmaceutically acceptable salt thereof, is about 10-200 mg. In some such embodiments, a therapeutically effective amount of taladegib, or a pharmaceutically acceptable salt thereof, is about 100-200 mg. In certain embodiments, the therapeutically effective amount of taladegib, or a pharmaceutically acceptable salt thereof, is about 100 mg. In some embodiments, the therapeutically effective amount of taladegib, or a pharmaceutically acceptable salt thereof, is about 100 mg administered once a day. In certain embodiments, the therapeutically effective amount of taladegib, or a pharmaceutically acceptable salt thereof, is about 150 mg. In some embodiments, the therapeutically effective amount of taladegib, or a pharmaceutically acceptable salt thereof, is about 150 mg administered once a day. In certain embodiments, the therapeutically effective amount of taladegib, or a pharmaceutically acceptable salt thereof, is about 200 mg. In some embodiments, the therapeutically effective amount of taladegib, or a pharmaceutically acceptable salt thereof, is about 200 mg administered once a day.

In some embodiments, provided methods comprise administering taladegib, or a pharmaceutically acceptable salt thereof, to a subject in need thereof once a day for at least 4 weeks, at least 8 weeks, at least 12 weeks, at least 16 weeks, at least 20 weeks, at least 24 weeks, or longer. In some embodiments, provided methods comprise administering taladegib, or a pharmaceutically acceptable salt thereof, to a subject in need thereof once a day for an extended period of time (e.g., 6 months, 12 months, 18 months, 24 months, 30 months, 36 months). In some embodiments, provided methods comprise administering taladegib, or a pharmaceutically acceptable salt thereof, to a subject in need thereof once a day for the remainder of the subject's life. In some embodiments, taladegib is administered as a unit dose. In some embodiments, a unit dose of taladegib is about 25 mg, about 50 mg, about 100 mg, or about 200 mg. In some embodiments, taladegib, or a pharmaceutically acceptable salt thereof, is administered to the subject until the symptoms of pulmonary fibrosis completely resolve or until symptoms of pulmonary fibrosis significantly resolve.

In some embodiments, the present disclosure provides a method of slowing progression of pulmonary fibrosis, the method comprising administering taladegib, or a pharmaceutically acceptable salt thereof, to a subject in need thereof. In some embodiments, the present disclosure provides a method of reversing pulmonary fibrosis, the method comprising administering taladegib, or a pharmaceutically acceptable salt thereof, to a subject in need thereof. In some such embodiments, the method comprises administering a therapeutically effective amount of taladegib, or a pharmaceutically acceptable salt thereof. In some such embodiments, a therapeutically effective amount of taladegib, or a pharmaceutically acceptable salt thereof, is about 10-200 mg. In some such embodiments, a therapeutically effective amount of taladegib, or a pharmaceutically acceptable salt thereof, is about 100-200 mg. In certain embodiments, the therapeutically effective amount of taladegib, or a pharmaceutically acceptable salt thereof, is about 100 mg. In some embodiments, the therapeutically effective amount of taladegib, or a pharmaceutically acceptable salt thereof, is about 100 mg administered once a day. In certain embodiments, the therapeutically effective amount of taladegib, or a pharmaceutically acceptable salt thereof, is about 150 mg. In some embodiments, the therapeutically effective amount of taladegib, or a pharmaceutically acceptable salt thereof, is about 150 mg administered once a day. In certain embodiments, the therapeutically effective amount of taladegib, or a pharmaceutically acceptable salt thereof, is about 200 mg. In some embodiments, the therapeutically effective amount of taladegib, or a pharmaceutically acceptable salt thereof, is about 200 mg administered once a day.

In some embodiments, the present disclosure provides a method of treating pulmonary fibrosis, wherein the method comprises administering to a subject in need thereof taladegib, or a pharmaceutically acceptable salt thereof, according to a treatment regimen that reduces pulmonary vascular volume. In some such embodiments, a treatment regimen that reduces pulmonary vascular volume comprises administering an amount of taladegib, or a pharmaceutically acceptable salt thereof, that is about 10-200 mg. In some such embodiments, a treatment regimen that reduces pulmonary vascular volume comprises administering an amount of taladegib, or a pharmaceutically acceptable salt thereof, that is about 100-200 mg. In certain embodiments, a treatment regimen that reduces pulmonary vascular volume comprises administering an amount of taladegib, or a pharmaceutically acceptable salt thereof, that is about 100 mg. In some embodiments, a treatment regimen that reduces pulmonary vascular volume comprises administering an amount of taladegib, or a pharmaceutically acceptable salt thereof, that is about 100 mg and the taladegib is administered once a day. In certain embodiments, a treatment regimen that reduces pulmonary vascular volume comprises administering an amount of taladegib, or a pharmaceutically acceptable salt thereof, that is about 150 mg. In some embodiments, a treatment regimen that reduces pulmonary vascular volume comprises administering an amount of taladegib, or a pharmaceutically acceptable salt thereof, that is about 150 mg and the taladegib is administered once a day. In certain embodiments, a treatment regimen that reduces pulmonary vascular volume comprises administering an amount of taladegib, or a pharmaceutically acceptable salt thereof, that is about 200 mg. In some embodiments, a treatment regimen that reduces pulmonary vascular volume comprises administering an amount of taladegib, or a pharmaceutically acceptable salt thereof, that is about 200 mg and the taladegib is administered once a day.

In some embodiments, the present disclosure provides a method of treating pulmonary fibrosis, wherein the method comprises administering to a subject in need thereof taladegib, or a pharmaceutically acceptable salt thereof, wherein pulmonary vascular volume is reduced. In some such embodiments, the method comprises administering an amount of taladegib, or a pharmaceutically acceptable salt thereof, that is about 10-200 mg. In some such embodiments, the method comprises administering an amount of taladegib, or a pharmaceutically acceptable salt thereof, that is about 100-200 mg. In certain embodiments, the method comprises administering an amount of taladegib, or a pharmaceutically acceptable salt thereof, that is about 100 mg. In some embodiments, the method comprises administering an amount of taladegib, or a pharmaceutically acceptable salt thereof, that is about 100 mg, wherein the taladegib is administered once a day. In certain embodiments, the method comprises administering an amount of taladegib, or a pharmaceutically acceptable salt thereof, that is about 150 mg. In some embodiments, the method comprises administering an amount of taladegib, or a pharmaceutically acceptable salt thereof, that is about 150 mg, wherein the taladegib is administered once a day. In certain embodiments, the method comprises administering an amount of taladegib, or a pharmaceutically acceptable salt thereof, that is about 200 mg. In some embodiments, the method comprises administering an amount of taladegib, or a pharmaceutically acceptable salt thereof, that is about 200 mg, wherein the taladegib is administered once a day.

In some embodiments, the present disclosure provides a method of reducing pulmonary vascular volume in a subject in need thereof, wherein the method comprises administering to the subject an effective amount of taladegib. In some such embodiments, the effective amount of taladegib is about 10-200 mg. In some such embodiments, the effective amount of taladegib is about 100-200 mg. In certain embodiments, the effective amount of taladegib is about 100 mg. In some embodiments, the effective amount of taladegib is about 100 mg once a day. In certain embodiments, the effective amount of taladegib is about 150 mg. In some embodiments, the effective amount of taladegib is about 150 mg administered once a day. In certain embodiments, the effective amount of taladegib is about 200 mg. In some embodiments, the effective amount of taladegib is about 200 mg administered once a day.

In some embodiments, the pulmonary fibrosis is idiopathic pulmonary fibrosis (IPF). In some embodiments, the pulmonary fibrosis is non-IPF progressive pulmonary fibrosis (PPF)

DETAILED DESCRIPTION

Definitions

Figure 1B:
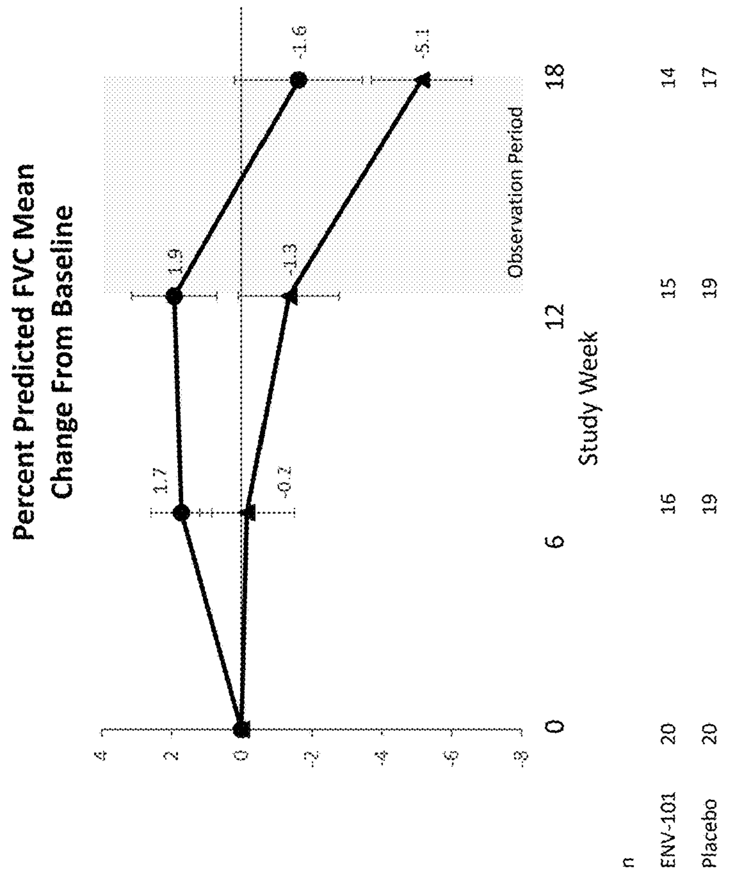
FIG. 1B is a graph that shows the mean change from baseline of percent predicted forced vital capacity (ppFVC) in IPF subjects treated with 200 mg QD taladegib (also known as ENV-101) (●) as compared to the placebo group (▲). At 6 weeks, the mean ppFVC for the treated group (n=16) was 1.7%, as compared to the mean FVC (mL) for the placebo group (n=19) of −0.2%. At 12 weeks, the mean ppFVC for the treated group (n=15) was 1.9%, as compared to the mean ppFVC for the placebo group (n=19) of −1.3% (p=0.035).

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Increased, Induced, or Reduced: As used herein, these terms or grammatically comparable comparative terms, indicate values that are relative to a comparable reference measurement. For example, in some embodiments, an assessed value achieved with a provided composition (e.g., a pharmaceutical composition) may be "increased" relative to that obtained with a comparable reference composition. Alternatively or additionally, in some embodiments, an assessed value achieved in a subject may be "increased" relative to that obtained in the same subject under different conditions (e.g., prior to or after an event; or presence or absence of an event such as administration of a composition (e.g., a pharmaceutical composition) as described herein, or in a different, comparable subject (e.g., in a comparable subject that differs from the subject of interest in prior exposure to a condition, e.g., absence of administration of a composition (e.g., a pharmaceutical composition) as described herein.). In some embodiments, comparative terms refer to statistically relevant differences (e.g., that are of a prevalence and/or magnitude sufficient to achieve statistical relevance). Those skilled in the art will be aware, or will readily be able to determine, in a given context, a degree and/or prevalence of difference that is required or sufficient to achieve such statistical significance. In some embodiments, the term "reduced" or equivalent terms refers to a reduction in the level of an assessed value by at least 5%, at least 10%, at least 20%, at least 50%, at least 75% or higher, as compared to a comparable reference. In some embodiments, the term "reduced" or equivalent terms refers to a complete or essentially complete inhibition, i.e., a reduction to zero or essentially to zero. In some embodiments, the term "increased" or "induced" refers to an increase in the level of an assessed value by at least 10%, at least 20%, at least 30%, at least 40%, at least 50%, at least 80%, at least 100%, at least 200%, at least 500%, or higher, as compared to a comparable reference.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences,* 66:1-19 (1977), incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Pharmaceutically acceptable carrier or diluent: The term "pharmaceutically acceptable carrier or diluent" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutical composition: As used herein, the term "pharmaceutical composition" refers to an active agent, formulated together with one or more pharmaceutically acceptable carriers. In some embodiments, the active agent is present in unit dose amount appropriate for administration in a therapeutic or dosing regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Subject: As used herein, the term "subject" refers to an organism to be administered with a composition described herein, e.g., for experimental, diagnostic, prophylactic, and/or therapeutic purposes. Typical subjects include animals (e.g., mammals such as mice, rats, rabbits, non-human primates, domestic pets, etc.) and humans. In some embodiments, a subject is a human subject. In some embodiments, a subject is suffering from a disease, disorder, or condition (e.g., a fibrotic condition such as pulmonary fibrosis). In some embodiments, a subject is susceptible to a disease, disorder, or condition (e.g., a fibrotic condition such as pulmonary fibrosis). In some embodiments, a subject displays one or more symptoms or characteristics of a disease, disorder, or condition (e.g., a fibrotic condition such as pulmonary fibrosis). In some embodiments, a subject displays one or more non-specific symptoms of a disease, disorder, or condition (e.g., a fibrotic condition such as pulmonary fibrosis). In some embodiments, a subject does not display any symptom or characteristic of a disease, disorder, or condition (e.g., a fibrotic condition such as pulmonary fibrosis). In some embodiments, a subject is someone with one or more features characteristic of susceptibility to or risk of a disease, disorder, or condition (e.g., a fibrotic condition such as pulmonary fibrosis). In some embodiments, a subject is a patient. In some embodiments, a subject is an individual to whom diagnosis and/or therapy is and/or has been administered.

Therapeutically effective amount: The term "therapeutically effective amount" refers to the amount which achieves a desired reaction or a desired effect alone or together with further doses. In the case of the treatment of a particular disease (e.g., a fibrotic condition such as pulmonary fibrosis), a desired reaction in some embodiments relates to inhibition of the course of the disease (e.g., a fibrotic condition such as pulmonary fibrosis). In some embodiments, such inhibition may comprise slowing down the progress of a disease (e.g., a fibrotic condition such as pulmonary fibrosis) and/or interrupting or reversing the progress of the disease (e.g., a fibrotic condition such as pulmonary fibrosis). In some embodiments, a desired reaction in a treatment of a disease (e.g., a fibrotic condition such as pulmonary fibrosis) may be or comprise delay or prevention of the onset of a disease (e.g., a fibrotic condition such as pulmonary fibrosis) or a condition (e.g., a fibrotic condition such as pulmonary fibrosis). An effective amount of a composition (e.g., a pharmaceutical composition) described herein will depend, for example, on disease (e.g., a fibrotic condition such as pulmonary fibrosis) or a condition (e.g., a fibrotic condition such as pulmonary fibrosis) to be treated, the severity of such a disease (e.g., a fibrotic condition such as pulmonary fibrosis) or a condition (e.g., a fibrotic condition such as pulmonary fibrosis), individual parameters of the patient, including, e.g., age, physiological condition, size and weight, the duration of treatment, the type of an accompanying therapy (if present), the specific route of administration and similar factors. Accordingly, doses of a composition (e.g., a pharmaceutical composition) described herein may depend on various of such parameters. In the case that a reaction in a patient is insufficient with an initial dose, higher doses (or effectively higher doses achieved by a different, more localized route of administration) may be used.

Treat or Treating: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition (e.g., a fibrotic condition such as pulmonary fibrosis). Treatment may be administered to a subject who does not exhibit signs of a disease, disorder, and/or condition (e.g., a fibrotic condition such as pulmonary fibrosis). In some embodiments, treatment may be administered to a subject who exhibits only early signs of the disease, disorder, and/or condition (e.g., a fibrotic condition such as pulmonary fibrosis), for example for the purpose of decreasing the risk of developing pathology associated with the disease, disorder, and/or condition. In some embodiments, treatment may be administered to a subject at a later-stage of disease, disorder, and/or condition (e.g., a fibrotic condition such as pulmonary fibrosis).

"Fibrosis" refers to the formation of excess fibrous connective tissue in an organ or tissue in a reparative or reactive process. Fibrosis is similar to the process called scarring, in that both involve stimulated fibroblasts laying down connective tissue, including collagen and glycosaminoglycans. The fibrosis can be initiated when immune cells such as macrophages release soluble factors that stimulate fibroblasts. The most well-characterized pro-fibrotic mediator can be TGF beta, which is released by macrophages as well as any damaged tissue between surfaces called interstitium.

Other soluble mediators of fibrosis include, but are not limited to, CTGF, platelet-derived growth factor (PDGF), and Interleukin 4 (IL-4). These molecules initiate signal transduction pathways such as the AKT/mTOR and SMAD pathways that ultimately lead to the proliferation and activation of fibroblasts, which deposit extracellular matrix into the surrounding connective tissue. This process of tissue repair can be a complex one, with tight regulation of ECM synthesis and degradation ensuring maintenance of normal tissue architecture. However, the entire process, although necessary, can lead to a progressive irreversible fibrotic response if tissue injury is severe or repetitive, or if the wound healing response itself becomes deregulated.

IPF is the most aggressive of interstitial lung diseases with survival of 2-3 years from time of diagnosis. IPF is a progressive fibrotic lung scarring disease that results in loss of lung elasticity, capacity, and function. Current therapeutic options are limited to drugs that modestly slow the rate of lung function decrease. Significant advances are required and urgently needed for patients.

The understanding of IPF has progressed greatly over the past decade with a clear understanding that the driver of the disease is a dysregulated tissue remodeling rather than inflammation. In essence, IPF is a chronic wound with characteristics identical to a wound healing process. These are processes driven by fibroblast activation and trans differentiation of cells into myofibroblasts which deposit fibrotic extracellular matrix and contract tissue. Of great interest is the dominant pathway that governs fibroblast activation and myofibroblast accumulation, the Hedgehog (Hh) pathway through activation of Smoothened (Smo).

Myofibroblasts are key cellular drivers for IPF. The initial step in IPF is injury of lung alveolar epithelial cells via environmental toxins or viral infection. Patients present with IPF long after the initial injury, so this causative step involving inflammation is generally unknown and inflammation is less relevant by the time of presentation. As part of the wound healing process after initial insult, Sonic Hedgehog (SHh) is secreted. SHh activates fibroblasts and initiates epithelial mesenchymal transition (EMT) leading to production and activation of myofibroblasts in a Smo-dependent manner. Myofibroblasts secrete collagen and other extracellular matrix (ECM) proteins by which they adhere to and contract tissue, ultimately pulling the lung closed (i.e., reducing lung elasticity, capacity and function) like a wound. The action of myofibroblasts is the primary cause of IPF pathology and therefore inhibition of the Hh pathway uniquely targets the driver of IPF disease.

Myofibroblasts are derived via EMT mediated by Hedgehog or transforming growth factor (TGF) in a Hedgehog-dependent fashion. Both SHh and TGF drive differentiation of fibroblasts and other cells into myofibroblasts in a process governed by Smo. This positive feedback loop becomes dysregulated in IPF resulting in accumulation of myofibroblasts. Increased production of intracellular alpha-smooth muscle actin ($\alpha$SMA) is a key characteristic of differentiated myofibroblasts and IPF fibrotic foci are rife with $\alpha$SMA.

Inhibition of Hedgehog results in apoptosis or deactivation of myofibroblasts. SHh and activation of the Hh pathway protect myofibroblasts from apoptosis, resulting in accumulation of the cellular driver of IPF. Disruption of the Hh pathway reduces the myofibroblast production of ECM such as collagen and intracellular $\alpha$SMA, both of which are required for contraction. Additionally, inhibition of Smo re-sensitizes myofibroblasts to apoptotic processes.

Hedgehog and myofibroblasts are upregulated in IPF patients. IPF patient lung samples have confirmed Hedgehog pathway components are upregulated and that myofibroblasts are significantly infiltrated. Normal lung samples are largely devoid of Hh pathway components or myofibroblasts.

In some embodiments, the present disclosure provides a method of treating pulmonary fibrosis, the method comprising administering taladegib, or a pharmaceutically acceptable salt thereof, to a subject in need thereof. In some such embodiments, the method comprises administering a therapeutically effective amount of taladegib, or a pharmaceutically acceptable salt thereof. In some such embodiments, a therapeutically effective amount of taladegib, or a pharmaceutically acceptable salt thereof, is about 10-200 mg. In some such embodiments, a therapeutically effective amount of taladegib, or a pharmaceutically acceptable salt thereof, is about 100-200 mg. In certain embodiments, the therapeutically effective amount of taladegib, or a pharmaceutically acceptable salt thereof, is about 100 mg. In some embodiments, the therapeutically effective amount of taladegib, or a pharmaceutically acceptable salt thereof, is about 100 mg administered once a day. In certain embodiments, the therapeutically effective amount of taladegib, or a pharmaceutically acceptable salt thereof, is about 150 mg. In some embodiments, the therapeutically effective amount of taladegib, or a pharmaceutically acceptable salt thereof, is about 150 mg administered once a day. In certain embodiments, the therapeutically effective amount of taladegib, or a pharmaceutically acceptable salt thereof, is about 200 mg. In some embodiments, the therapeutically effective amount of taladegib, or a pharmaceutically acceptable salt thereof, is about 200 mg administered once a day.

In some embodiments, the present disclosure provides a method of improving lung function in a subject suffering from or diagnosed with pulmonary fibrosis, for example, idiopathic pulmonary fibrosis (IPF) or non-IPF progressive pulmonary fibrosis (PPF), the method comprising administering taladegib, or a pharmaceutically acceptable salt thereof, to the subject. In some such embodiments, the method comprises administering a therapeutically effective amount of taladegib, or a pharmaceutically acceptable salt thereof. In some such embodiments, a therapeutically effective amount of taladegib, or a pharmaceutically acceptable salt thereof, is about 10-200 mg. In some such embodiments, a therapeutically effective amount of taladegib, or a pharmaceutically acceptable salt thereof, is about 100-200 mg. In certain embodiments, the therapeutically effective amount of taladegib, or a pharmaceutically acceptable salt thereof, is about 100 mg. In some embodiments, the therapeutically effective amount of taladegib, or a pharmaceutically acceptable salt thereof, is about 100 mg administered once a day. In certain embodiments, the therapeutically effective amount of taladegib, or a pharmaceutically acceptable salt thereof, is about 150 mg. In some embodiments, the therapeutically effective amount of taladegib, or a pharmaceutically acceptable salt thereof, is about 150 mg administered once a day. In certain embodiments, the therapeutically effective amount of taladegib, or a pharmaceutically acceptable salt thereof, is about 200 mg. In some embodiments, the therapeutically effective amount of taladegib, or a pharmaceutically acceptable salt thereof, is about 200 mg administered once a day.

In some embodiments, the improvement in lung function is continuous improvement during the treatment period (i.e., during the period in which the subject is administered taladegib). In some embodiments, the improvement in lung function is maintained or persists after the treatment period (i.e., after the period in which the subject was administered taladegib).

In some embodiments, the improvement in lung function is determined by an improvement in forced vital capacity (FVC) as compared to baseline FVC (e.g., a change from baseline of FVC measured in mL at week 12). In some embodiments, the present disclosure provides a method of increasing forced vital capacity in a subject in need thereof, the method comprising administering 200 mg taladegib, or a pharmaceutically acceptable salt thereof, to the subject. In some embodiments, the forced vital capacity is increased by about 40 mL, about 50 mL, about 60 mL, about 70 mL, about 80 mL, about 90 mL or about 100 mL. In some embodiments, the forced vital capacity is increased by at least 40 mL, at least 50 mL, at least 60 mL, at least 70 mL, at least 80 mL, at least 90 mL, or at least 100 mL. In some embodiments, the forced vital capacity (FVC) is percent predicted forced vital capacity (ppFVC).

In some embodiments, the improvement in lung function is determined by improvement in diffusion capacity of the lungs for carbon monoxide ($DL_{CO}$) as compared to baseline $DL_{CO}$ (e.g., a change from baseline in $DL_{CO}$, e.g., as measured at week 12).

In some embodiments, the improvement in lung function is determined by patient-reported outcomes, for example, as those reported by patients on the University of California San Diego Shortness of Breath Questionnaire (UCSD SOBQ) at, for example, week 12.)

In some embodiments, the improvement in lung function is determined by quantitative measurements or qualitative measurements.

In some embodiments, the improvement in lung function is determined by an increase in total lung capacity (TLC) as compared to baseline TLC. In some such embodiments, the improvement in lung capacity (TLC) is measured by high resolution CT (HRCT). In some embodiments, the present disclosure provides a method of increasing total lung capacity by about 5%, about 6%, about 7%, about 8%, about 9%, about 10%, about 11%, about 12%, about 13%, about 14%, or about 15% from baseline, the method comprising administering 200 mg taladegib, or a pharmaceutically acceptable salt thereof, to a subject in need thereof. In some embodiments, the present disclosure provides a method of increasing total lung capacity by at least 5%, at least 6%, at least 7%, at least 8%, at least 9%, at least 10%, at least 11%, at least 12%, at least 13%, at least 14%, or at least 15% from baseline, the method comprising administering 200 mg taladegib, or a pharmaceutically acceptable salt thereof, to a subject in need thereof.

In some embodiments, the present disclosure provides a method of increasing total lung capacity by about 50 mL, about 75 mL, about 100 mL, about 125 mL, about 150 mL, about 175 mL, about 200 mL, about 225 mL, about 250 mL, about 275 mL, or about 300 mL from baseline, the method comprising administering 200 mg taladegib, or a pharmaceutically acceptable salt thereof, to a subject in need thereof. In some embodiments, the present disclosure provides a method of increasing total lung capacity by at least 50 mL, at least 75 mL, at least 100 mL, at least 125 mL, at least 150 mL, at least 175 mL, at least 200 mL, at least 225 mL, at least 250 mL, at least 275 mL, or at least 300 mL from baseline, the method comprising administering 200 mg taladegib, or a pharmaceutically acceptable salt thereof, to a subject in need thereof.

In some embodiments, the improvement in lung function is determined by a reduction in one or measures of lung fibrosis. In some embodiments, the one or more measures of fibrosis are selected from percent quantitative lung fibrosis (% QLF), percent ground glass opacity, or percent honeycombing.

In some embodiments, the present disclosure provides a method of improving quantitative lung fibrosis (QLF) in a subject in need thereof, the method comprising administering 200 mg taladegib, or a pharmaceutically acceptable salt thereof, to the subject. In some embodiments, the subject experiences a change from baseline % QLF of about −0.5%, about −0.6%, about −0.7%, about −0.8%, about −0.9%, about −1.0%, about −1.1%, about −1.2%, about −1.3%, about −1.4%, about −1.5%, about −1.6%, about −1.7%, about −1.8%, about −1.9%, about −2.0%, about −2.1%, about −2.2%, about −2.3%, about −2.4%, about −2.5%, about −2.6%, about −2.7%, about −2.8%, about −2.9%, or about −3.0%. In some embodiments, the subject experiences a change from baseline % QLF of at least −0.5%, at least −0.6%, at least −0.7%, at least −0.8%, at least −0.9%, at least −1.0%, at least −1.1%, at least −1.2%, at least −1.3%, at least −1.4%, at least −1.5%, at least −1.6%, at least −1.7%, at least −1.8%, at least −1.9%, at least −2.0%, at least −2.1%, at least −2.2%, at least −2.3%, at least −2.4 at least −2.5%, at least −2.6%, at least −2.7%, at least −2.8%, at least −2.9%, at least −3.0%.

In some embodiments, the present disclosure provides a method of improving or reducing percent quantitative interstitial lung disease (% QILD) in a subject in need thereof, the method comprising administering 200 mg taladegib, or a pharmaceutically acceptable salt thereof, to the subject. In some embodiments, the subject experiences a change from baseline % QILD of about −0.5%, about −1.0%, about −1.5%, about −2.0%, about −2.5%, about −3.0%, about −3.5%, about −4.0%, about −4.5%, about −5.0%, about −5.5%, about −6.0%, about −6.5%, about −7.0%, about −7.5%, about −8.0%, about −8.5%, about −9.0%, about −9.5%, about −10.0%, about −10.5%, about −11.0%, about −11.5%, about −12.0%, about −12.5%, or about −13.0%. In some embodiments, the subject experiences a change from baseline % QILD of at least −0.5%, at least −1.0%, at least −1.5%, at least −2.0%, at least −2.5%, at least −3.0%, at least −3.5%, at least −4.0%, at least −4.5%, at least −5.0%, at least −5.5%, at least −6.0%, at least −6.5%, at least −7.0%, at least −7.5%, at least −8.0%, at least −8.5%, at least −9.0%, at least −9.5%, at least −10.0%, at least −10.5%, at least −11.0%, at least −11.5%, at least −12.0%, at least −12.5%, or at least −13.0%.

In some embodiments, the present disclosure provides a method of improving percent quantitative ground glass opacity (% QGG) in a subject in need thereof, the method comprising administering 200 mg taladegib, or a pharmaceutically acceptable salt thereof, to the subject. In some embodiments, the subject experiences a change from baseline % QGG of about −0.5%, about −1.0%, about −1.5%, about −2.0%, about −2.5%, about −3.0%, about −3.5%, about −4.0%, about −4.5%, about −5.0%, about −5.5%, about −6.0%, about −6.5%, about −7.0%, about −7.5%, about −8.0%, about −8.5%, about −9.0%, about −9.5%, or about −10.0%. In some embodiments, the subject experiences a percent change from baseline QGG of at least −0.5%, at least −1.0%, at least −1.5%, at least −2.0%, at least −2.5%, at least −3.0%, at least −3.5%, at least −4.0%, at least −4.5%, at least −5.0%, at least −5.5%, at least −6.0%, at least −6.5%, at least −7.0%, at least −7.5%, at least −8.0%, at least −8.5%, at least −9.0%, at least −9.5%, or at least −10.0%.

In some embodiments, the improvement in lung function is measured by quantitative appearance such as reduction in scarring of the lung tissue or reduction in remodeling of the lung tissue as measured by an imaging technique such as CT scan or MRI.

In some embodiments, a subject administered taladegib, or a pharmaceutically acceptable salt thereof, does not experience any grade 4 adverse events. In some embodiments, a subject administered taladegib does not experience any grade 3 or grade 4 adverse events.

In some embodiments, the present disclosure provides a method comprising:

a. administering an initial dose of taladegib, or a pharmaceutically acceptable salt thereof, to a subject in need thereof; and
b. if the subject experiences one or more adverse events, decreasing the dose of taladegib (i.e., a "step-down dose").

In some embodiments, the subject is administered a step-down dose until the adverse event resolves. In some embodiments, the subject resumes the initial dose (e.g., 200 mg) once the adverse event has resolved. In some embodiments, an initial dose is 50 mg, 75 mg, 100 mg, 125 mg, 150 mg, 175 mg, or 200 mg. In some embodiments, a step-down dose is 25 mg. In some embodiments, a step-down dose is 50 mg. In some embodiments, a step-down dose is 75 mg. In some embodiments, a step-down dose is 100 mg. In some embodiments, a step-down dose is 125 mg. In some embodiments, a step-down dose is 150 mg. In some embodiments, a step-down dose is 175 mg.

In some embodiments, the present disclosure provides a method comprising:

a. administering an initial dose of taladegib, or a pharmaceutically acceptable salt thereof, to a subject in need thereof; and
b. if the subject experiences one or more adverse events, decreasing the dose of taladegib to a first step-down dose.

In some embodiments, if the subject continues to experience one or more adverse events, further decreasing the dose of taladegib to a second step-down dose. In some embodiments, a first step-down dose is half of the initial dose, and the second step-down dose is half of the first step-down dose. For example, in some embodiments, an initial dose is 200 mg, a first step-down dose is 100 mg, and a second step-down dose is 50 mg. In some embodiments, a first step-down dose is a 50 mg decrement, and the second dose is a further 50 mg decrement. For example, in some embodiments, an initial dose is 200 mg, a first step-down dose is 150 mg, and a second step-down dose is 100 mg. In some embodiments, a first step-down dose is 150mg. In some embodiments, a second step-down dose is 100 mg. In some embodiments, if the subject is administered a first step-down dose, the subject resumes the initial dose (e.g., 200 mg) once the adverse event resolves. In some embodiments, if the subject is administered a second step-down dose, the subject resumes the first step-down dose for a period of time sufficient to ensure that the one or more adverse events do not resume. In some embodiments, the subject resumes the first step-down dose for a period of 1 week, 2 weeks, 3 weeks, 4 weeks, 5 weeks, 6 weeks, 7 weeks, or 8 weeks.

In some embodiments, the present disclosure provides a method of treating pulmonary fibrosis, the method comprising administering 200 mg taladegib, or a pharmaceutically acceptable salt thereof, to a subject in need thereof once a day for at least 4 weeks, at least 8 weeks, at least 12 weeks, at least 16 weeks, at least 20 weeks, at least 24 weeks, or longer. In some embodiments, taladegib, or a pharmaceutically acceptable salt thereof, is administered to the subject until the symptoms of pulmonary fibrosis completely resolve or until symptoms of pulmonary fibrosis substantially resolve.

In some embodiments, the present disclosure provides a method of slowing progression of pulmonary fibrosis, the method comprising administering taladegib, or a pharmaceutically acceptable salt thereof, to a subject in need thereof. In some embodiments, the present disclosure provides a method of reversing pulmonary fibrosis, the method comprising administering taladegib, or a pharmaceutically acceptable salt thereof, to a subject in need thereof. In some such embodiments, the method comprises administering a therapeutically effective amount of taladegib, or a pharmaceutically acceptable salt thereof. In some such embodiments, a therapeutically effective amount of taladegib, or a pharmaceutically acceptable salt thereof, is about 10-200 mg. In some such embodiments, a therapeutically effective amount of taladegib, or a pharmaceutically acceptable salt thereof, is about 100-200 mg. In certain embodiments, the therapeutically effective amount of taladegib, or a pharmaceutically acceptable salt thereof, is about 100 mg. In some embodiments, the therapeutically effective amount of taladegib, or a pharmaceutically acceptable salt thereof, is about 100 mg administered once a day. In certain embodiments, the therapeutically effective amount of taladegib, or a pharmaceutically acceptable salt thereof, is about 150 mg. In some embodiments, the therapeutically effective amount of taladegib, or a pharmaceutically acceptable salt thereof, is about 150 mg administered once a day. In certain embodiments, the therapeutically effective amount of taladegib, or a pharmaceutically acceptable salt thereof, is about 200 mg. In some embodiments, the therapeutically effective amount of taladegib, or a pharmaceutically acceptable salt thereof, is about 200 mg administered once a day.

In some embodiments, the extent of fibrosis is determined by change from baseline of percent quantitative interstitial lung disease (% QILD). In some embodiments, the extent of fibrosis is determined by change from baseline of percent quantitative lung fibrosis (% QLF). In some embodiments, the extent of fibrosis is determined by change from baseline of percent quantitative ground glass opacity (% QGG).

In some embodiments, the present disclosure provides a method of treating pulmonary fibrosis, wherein the method comprises administering to a subject in need thereof taladegib, or a pharmaceutically acceptable salt thereof, according to a treatment regimen that reduces pulmonary vascular volume. In some such embodiments, a treatment regimen that reduces pulmonary vascular volume comprises administering an amount of taladegib, or a pharmaceutically acceptable salt thereof, that is about 10-200 mg. In certain embodiments, a treatment regimen that reduces pulmonary vascular volume comprises administering an amount of taladegib, or a pharmaceutically acceptable salt thereof, that is about 25 mg. In certain embodiments, a treatment regimen that reduces pulmonary vascular volume comprises administering an amount of taladegib, or a pharmaceutically acceptable salt thereof, that is about 50 mg. In some such embodiments, a treatment regimen that reduces pulmonary vascular volume comprises administering an amount of taladegib, or a pharmaceutically acceptable salt thereof, that is about 100-200 mg. In certain embodiments, a treatment regimen that reduces pulmonary vascular volume comprises administering an amount of taladegib, or a pharmaceutically acceptable salt thereof, that is about 100 mg. In some embodiments, a treatment regimen that reduces pulmonary vascular volume comprises administering an amount of taladegib, or a pharmaceutically acceptable salt thereof, that is about 100 mg and the taladegib administered once a day. In certain embodiments, a treatment regimen that reduces pulmonary vascular volume comprises administering an amount of taladegib, or a pharmaceutically acceptable salt thereof, that is about 150 mg. In some embodiments, a treatment regimen that reduces pulmonary vascular volume comprises administering an amount of taladegib, or a pharmaceutically acceptable salt thereof, that is about 150 mg and the taladegib is administered once a day. In certain embodiments, a treatment regimen that reduces pulmonary vascular volume comprises administering an amount of taladegib, or a pharmaceutically acceptable salt thereof, that is about 200 mg. In some embodiments, a treatment regimen that reduces pulmonary vascular volume comprises administering an amount of taladegib, or a pharmaceutically acceptable salt thereof, that is about 200 mg and the taladegib is administered once a day.

In some embodiments, the present disclosure provides a method of treating pulmonary fibrosis, wherein the method comprises administering to a subject in need thereof taladegib, or a pharmaceutically acceptable salt thereof, wherein pulmonary vascular volume is reduced. In some such embodiments, the method comprises administering an amount of taladegib, or a pharmaceutically acceptable salt thereof, that is about 10-200 mg. In certain embodiments, the method comprises administering an amount of taladegib, or a pharmaceutically acceptable salt thereof, that is about 25 mg. In certain embodiments, the method comprises administering an amount of taladegib, or a pharmaceutically acceptable salt thereof, that is about 50 mg. In some such embodiments, the method comprises administering an amount of taladegib, or a pharmaceutically acceptable salt thereof, that is about 100-200 mg. In certain embodiments, the method comprises administering an amount of taladegib, or a pharmaceutically acceptable salt thereof, that is about 100 mg. In some embodiments, the method comprises administering an amount of taladegib, or a pharmaceutically acceptable salt thereof, that is about 100 mg, wherein the taladegib is administered once a day. In certain embodiments, the method comprises administering an amount of taladegib, or a pharmaceutically acceptable salt thereof, that is about 150 mg. In some embodiments, the method comprises administering an amount of taladegib, or a pharmaceutically acceptable salt thereof, that is about 150 mg, wherein the taladegib is administered once a day. In certain embodiments, the method comprises administering an amount of taladegib, or a pharmaceutically acceptable salt thereof, that is about 200 mg. In some embodiments, the method comprises administering an amount of taladegib, or a pharmaceutically acceptable salt thereof, that is about 200 mg, wherein the taladegib is administered once a day.

In some embodiments, the present disclosure provides a method of reducing pulmonary vascular volume in a subject in need thereof, wherein the method comprises administering to the subject an effective amount of taladegib. In some such embodiments, the effective amount of taladegib is about 10-200 mg. In certain embodiments, the effective amount of taladegib is about 25 mg. In certain embodiments, the effective amount of taladegib is about 50 mg. In some such embodiments, the effective amount of taladegib is about 100-200 mg. In certain embodiments, the effective amount of taladegib is about 100 mg. In some embodiments, the effective amount of taladegib is about 100 mg administered once a day. In certain embodiments, the effective amount of taladegib is about 150 mg. In some embodiments, the effective amount of taladegib is about 150 mg administered once a day. In certain embodiments, the effective amount of taladegib is about 200 mg. In some embodiments, the effective amount of taladegib is about 200 mg administered once a day.

In some embodiments, a subject experiences a reduction in pulmonary vascular volume that is a change from baseline pulmonary vascular volume of about −0.01 percentage points, −0.03 percentage points, about −0.05 percentage points, about −0.10 percentage points, about −0.15 percentage points, about −0.20 percentage points, about −0.25 percentage points, about −0.30 percentage points, about −0.35 percentage points, about −0.40 percentage points, about −0.45 percentage points, about −0.50 percentage points, about −0.55 percentage points, about −0.60 percentage points, about −0.65 percentage points, about −0.70 percentage points, or about −0.75 percentage points. In some embodiments, a subject experiences a reduction in pulmonary vascular volume that is a change from baseline pulmonary vascular volume of about −0.05 percentage points, about −0.10 percentage points, about −0.15 percentage points, about −0.20 percentage points, about −0.25 percentage points, about −0.30 percentage points, about −0.35 percentage points, about −0.40 percentage points, about −0.45 percentage points, about −0.50 percentage points, about −0.55 percentage points, about −0.60 percentage points, or about −0.65 percentage points. In some embodiments, a subject experiences a reduction in pulmonary vascular volume that is a change from baseline pulmonary vascular volume of at least −0.05 percentage points, at least −0.10 percentage points, at least −0.15 percentage points, at least −0.20 percentage points, at least −0.25 percentage points, at least −0.30 percentage points, at least −0.35 percentage points, at least −0.40 percentage points, at least −0.45 percentage points, at least −0.50 percentage points, at least −0.55 percentage points, at least −0.60 percentage points, or at least −0.65 percentage points.

In some embodiments, the pulmonary fibrosis is idiopathic pulmonary fibrosis (IPF). In some embodiments, the pulmonary fibrosis is non-IPF progressive pulmonary fibrosis (PPF).

In some embodiments, provided methods comprise administering to a subject who is not concurrently exposed to one or more agents selected from N-acetylcysteine, an endothelin receptor antagonist, riociguat, prostacyclin or a prostacyclin analog, warfarin, a cytotoxic agent (e.g., colchicine), radiation to the lungs, an immunosuppressive agent (e g., methotrexate, azathioprine, etc.), a glucocorticosteroid, and an antifibrotic agent (e.g., nintedanib, pirfenidone, etc.).

In some embodiments, provided methods comprise administering taladegib, or a pharmaceutically acceptable salt thereof, to a subject who has previously been treated with nintedanib (Ofev®) or pirfenidone (Esbriet®). In some embodiments, provided methods comprise administering taladegib, or a pharmaceutically acceptable salt thereof, to a subject who has not been previously treated with nintedanib (Ofev®) or pirfenidone (Esbriet®). In some embodiments, a subject treated with taladegib does not have confirmed active human immunodeficiency virus (HIV), Hepatitis B virus (HBV) or Hepatitis C virus (HCV).

In some embodiments, a subject treated with taladegib, or a pharmaceutically acceptable salt thereof, is not concurrently exposed to a moderate or strong CYP3A4 inhibitor. In some embodiments, a moderate inhibitor of CYP3A4 is selected from amiodarone, erythromycin, fluconazole, miconazole, diltiazem, verapamil, delavirdine, amprenavir, fosamprenavir, and conivaptan, among others. In some embodiments, a strong CYP3A4inhibitor is selected from boceprevir, clarithromycin, conivaptan, grapefruit juice, itraconazole, ketoconazole, indinavir, lopinavir/ritonavir combination, mibefradil, nefazodone, nelfinavir, Posaconazole, ritonavir, saquinavir, telaprevir, telithromycin, and voriconazole, among others.

In some embodiments, taladegib, or a pharmaceutically acceptable salt thereof, is administered as an oral dosage form, for example, as a capsule or tablet In some embodiments, a tablet further comprises one or more pharmaceutically acceptable carriers selected from polymers, disintegrants, glidants, lubricants, coatings, binders, flavorants, etc.

In some embodiments, a disintegrant is selected from, for example, sodium starch gycolate, sodium alginate, alginic acid, amberlite, methyl cellulose, croscarmellose sodium.

In some embodiments, a glidant is selected from, for example, colloidal silica, cornstarch, talc, combinations thereof, or the like.

In some embodiments, a glidant is selected from, for example, a lubricant is selected from magnesium stearate, sodium stearyl fumarate, calcium stearate, stearic acid, zinc stearate combinations thereof, or the like.

In some embodiments, a film coating is selected from hydroxyethyl cellulose, hydroxypropyl cellulose, hydroxypropyl methyl cellulose, methyl cellulose, ethyl cellulose, polyvinyl alcohol, OPADRY®, combinations thereof, or the like.

In some embodiments, a binder is selected from acacia, alginic acid, methyl cellulose, carboxymethyl cellulose sodium, compressible sugar (Nu-Tab), microcrystalline cellulose, ethyl cellulose, gelatin, povidone, starch, and gums such as guar gum, tragacanth, combinations thereof, or the like.

In some embodiments, a flavorant is selected from acacia syrup, aromatic elixir, cherry syrup, cocoa syrup, orange syrup, combinations thereof, or the like.

In some embodiments, a unit dose (i.e., each dose of taladegib) or unit dosage form contains from about 15 mg to about 1000 mg, from about 25 mg to about 750 mg, from about 50 mg to about 500 mg, from about 50 mg to about 400 mg, from about 50 mg to about 300 mg, from about 50 mg to about 250 mg, from about 100 mg to about 200 mg, from about 25 mg to about 200 mg, about 25 mg, about 35 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, or about 250 mg of taladegib, or a pharmaceutically acceptable salt thereof. It will be appreciated that the amount of taladegib in a unit dosage form is the amount of the free base of taladegib and not the amount of a particular salt of taladegib. For example, a tablet comprising "200 mg taladegib" comprises 200 mg of the free base form of taladegib. If taladegib were provided as an HCl salt, the amount of taladegib●HCl in a "200 mg tablet" would be about 214 mg.

In some embodiments, the herein disclosed compounds of can be formulated as tablets containing 25, 50, 100, 150, 200, 250, 300, or 350 mg of taladegib and one or more pharmaceutical ingredients selected from croscarmellose sodium, HPMCAS-H, mannitol, microcrystalline cellulose, silicon dioxide, and sodium stearyl fumarate. One particular embodiment contains about 16.1% taladegib, about 37.6% HPMCAS-H, about 9.3% mannitol, about 28.6% microcrystalline cellulose, about 2.9% croscarmellose sodium, about 1.0% silicon dioxide, about 1.2% sodium stearyl fumarate, and about 3.4% OPADRY® (Film Coating). In some embodiments, a tablet for use in a method provided herein comprises between 5 and 25% of taladegib, between 20 and 50% HPMCAS-H, between 15 and 45% mannitol, between 15 and 45% microcrystalline cellulose, between 1 and 5% croscarmellose sodium, between 0.5 and 5% silicon dioxide, between 0.5 and 5% sodium stearyl fumarate, and between 1 and 10% OPADRY®.

EXEMPLARY EMBODIMENTS

1. A method of treating fibrosis comprising administering means for inhibiting Gli1.
2. The method of Embodiment 1, comprising administering a compound of Formula I:

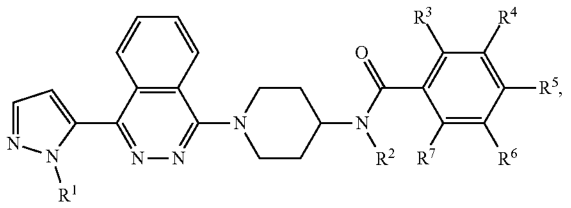

or a pharmaceutically acceptable salt thereof, wherein:

$R^1$ is hydrogen or methyl;

$R^2$ is hydrogen or methyl; and $R^3$, $R^4$, $R^5$, $R^6$, or $R^7$ are independently hydrogen, fluoro, chloro, cyano, trifluoromethyl, trifluoromethoxy, difluoromethoxy, methylsulfonyl, or trifluoromethylsulfonyl, provided that at least three of $R^3$, $R^4$, $R^5$, $R^6$, and $R^7$ are hydrogen.

3. The method of Embodiment 2 comprising administering taladegib.
4. The method of any one of Embodiments 1-3, comprising administering in doses from about 15 mg to about 1000 mg, from about 50 mg to about 500 mg, from about 50 mg to about 400 mg, from about 50 mg to about 300 mg, from about 50 mg to about 250 mg, from about 100 mg to about 200 mg, about 50 mg, about 100 mg, about 150 mg, about 200 mg, about 250 mg of said means or compound.
5. The method of any one of Embodiments 1-4, wherein the fibrosis is progressive pulmonary fibrosis.
6. The method of Embodiment 5, wherein the fibrosis is idiopathic pulmonary fibrosis.
7. A method of treating pulmonary fibrosis, the method comprising administering taladegib, or a pharmaceutically acceptable salt thereof, to a subject in need thereof.
8. A method of inducing apoptosis of myofibroblasts in a subject in need thereof, the method comprising administering taladegib, or a pharmaceutically acceptable salt thereof, to the subject.
9. A method of slowing progression of pulmonary fibrosis, the method comprising administering taladegib, or a pharmaceutically acceptable salt thereof, to a subject in need thereof.
10. A method of reversing pulmonary fibrosis, the method comprising administering taladegib, or a pharmaceutically acceptable salt thereof, to a subject in need thereof.
11. A method of improving lung function in a subject suffering from or diagnosed with pulmonary fibrosis, the method comprising administering taladegib, or a pharmaceutically acceptable salt thereof, to the subject.
12. The method according to Embodiment 11, wherein the improvement in lung function is continuous improvement during the period in which the subject is administered taladegib.
13. The method according to Embodiment 11, wherein the improvement in lung function is maintained or persists after the period in which the subject was administered taladegib.
14. The method according to Embodiment 11, wherein the improvement in lung function is determined by an improvement in forced vital capacity (FVC) as compared to baseline FVC (e.g., a change from baseline of FVC measured in mL).
15. The method according to Embodiment 14, wherein the forced vital capacity is increased by about 40 mL, about 50 mL, about 60 mL, about 70 mL, about 80 mL, about 90 mL or about 100 mL. In some embodiments, the forced vital capacity is increased by at least 40 mL, at least 50 mL, at least 60 mL, at least 70 mL, at least 80 mL, at least 90 mL, or at least 100 mL.
16. The method according to Embodiment 15, wherein the forced vital capacity (FVC) is percent predicted forced vital capacity (ppFVC).
17. The method according to Embodiment 11, wherein the improvement in lung function is determined by improvement in diffusion capacity of the lungs for carbon monoxide ($DL_{CO}$) as compared to baseline $DL_{CO}$ (e.g., a change from baseline in $DL_{CO}$).
18. The method according to Embodiment 11, wherein the improvement in lung function is determined by patient-reported outcomes, for example, as those reported by patients on the University of California San Diego Shortness of Breath Questionnaire (UCSD SOBQ).
19. The method according to Embodiment 11, wherein the improvement in lung function is determined by an increase in total lung capacity (TLC) as compared to baseline TLC.
20. The method according to Embodiment 19, wherein TLC is measured by high resolution CT (HRCT).
21. The method according to Embodiment 19 or Embodiment 20, wherein TLC is increased by about 5%, about 6%, about 7%, about 8%, about 9%, about 10%, about 11%, about 12%, about 13%, about 14%, or about 15% from baseline.
22. The method according to Embodiment 19 or Embodiment 20, wherein TLC is increased by at least 5%, at least 6%, at least 7%, at least 8%, at least 9%, at least 10%, at least 11%, at least 12%, at least 13%, at least 14%, or at least 15% from baseline.
23. The method according to Embodiment 19 or Embodiment 20, wherein TLC is increased by about 50 mL, about 75 mL, about 100 mL, about 125 mL, about 150 mL, about 175 mL, about 200 mL, about 225 mL, about 250 mL, about 275 mL, or about 300 mL from baseline.
24. The method according to Embodiment 19 or Embodiment 20, wherein TLC is increased by at least 50 mL, at least 75 mL, at least 100 mL, at least 125 mL, at least 150 mL, at least 175 mL, at least 200 mL, at least 225 mL, at least 250 mL, at least 275 mL, or at least 300 mL from baseline.
25. The method according to Embodiment 11, wherein the improvement in lung function is determined by a reduction in one or measures of lung fibrosis.
26. The method according to Embodiment 11, wherein the improvement in lung function is determined by an increase in lung volume.
27. The method according to any one of Embodiments 7 or 9-26, wherein the pulmonary fibrosis is idiopathic pulmonary fibrosis (IPF) or non-IPF progressive pulmonary fibrosis (PPF).
28. The method according to any one of Embodiments 7-27, wherein a total daily dose of taladegib is about 10-200 mg.
29. The method according to any one of Embodiments 7-27, wherein a total daily dose of taladegib is about 100-200 mg.
30. The method according to any one of Embodiments 7-27, wherein a total daily dose of taladegib is about 200 mg.

31. A method of improving percent quantitative lung fibrosis (% QLF) in a subject in need thereof, the method comprising administering 200 mg taladegib, or a pharmaceutically acceptable salt thereof, to the subject.
32. The method according to Embodiment 31, wherein the improvement in % QLF is the change from baseline % QLF of about −0.5%, about −0.6%, about −0.7%, about −0.8%, about −0.9%, about −1.0%, about −1.1%, about −1.2%, about −1.3%, about −1.4%, about −1.5%, about −1.6%, about −1.7%, about −1.8%, about −1.9%, about −2.0%, about −2.1%, about −2.2%, about −2.3%, about −2.4%, about −2.5%, about −2.6%, about −2.7%, about −2.8%, about −2.9%, or about −3.0%.
33. The method according to Embodiment 31, wherein the improvement in % QLF is the change from baseline % QLF of at least −0.5%, at least −0.6%, at least −0.7%, at least −0.8%, at least −0.9%, at least −1.0%, at least −1.1%, at least −1.2%, at least −1.3%, at least −1.4%, at least −1.5%, at least −1.6%, at least −1.7%, at least −1.8%, at least −1.9%, at least −2.0%, at least −2.1%, at least −2.2%, at least −2.3%, at least −2.4 at least −2.5%, at least −2.6%, at least −2.7%, at least −2.8%, at least −2.9%, at least −3.0%.
34. A method of improving or reducing percent quantitative interstitial lung disease (% QILD) in a subject in need thereof, the method comprising administering 200 mg taladegib, or a pharmaceutically acceptable salt thereof, to the subject.
35. The method according to Embodiment 34, wherein the improvement or reduction in % QILD is the change from baseline % QILD of about −0.5%, about −1.0%, about −1.5%, about −2.0%, about −2.5%, about −3.0%, about −3.5%, about −4.0%, about −4.5%, about −5.0%, about −5.5%, about −6.0%, about −6.5%, about −7.0%, about −7.5%, about −8.0%, about −8.5%, about −9.0%, about −9.5%, about −10.0%, about −10.5%, about −11.0%, about −11.5%, about −12.0%, about −12.5%, or about −13.0%.
36. The method according to Embodiment 34, wherein the improvement or reduction in % QILD is the change from baseline % QILD of at least −0.5%, at least −1.0%, at least −1.5%, at least −2.0%, at least −2.5%, at least −3.0%, at least −3.5%, at least −4.0%, at least −4.5%, at least −5.0%, at least −5.5%, at least −6.0%, at least −6.5%, at least −7.0%, at least −7.5%, at least −8.0%, at least −8.5%, at least −9.0%, at least −9.5%, at least −10.0%, at least −10.5%, at least −11.0%, at least −11.5%, at least −12.0%, at least −12.5%, or at least −13.0%.
37. A method of improving percent quantitative ground glass opacity (% QGG) in a subject in need thereof, the method comprising administering 200 mg taladegib, or a pharmaceutically acceptable salt thereof, to the subject.
38. The method according to Embodiment 37, wherein the improvement in % QGG is the change from baseline % QGG of about −0.5%, about −1.0%, about −1.5%, about −2.0%, about −2.5%, about −3.0%, about −3.5%, about −4.0%, about −4.5%, about −5.0%, about −5.5%, about −6.0%, about −6.5%, about −7.0%, about −7.5%, about −8.0%, about −8.5%, about −9.0%, about −9.5%, or about −10.0%.
39. The method according to Embodiment 37, wherein the improvement in % QGG is the change from baseline % QGG of at least −0.5%, at least −1.0%, at least −1.5%, at least −2.0%, at least −2.5%, at least −3.0%, at least −3.5%, at least −4.0%, at least −4.5%, at least −5.0%, at least −5.5%, at least −6.0%, at least −6.5%, at least −7.0%, at least −7.5%, at least −8.0%, at least −8.5%, at least −9.0%, at least −9.5%, or at least −10.0%.
40. The method according to any one of the preceding Embodiments, wherein taladegib is administered as one or more unit doses.
41. The method according to Embodiment 40, wherein the unit dose is about 25 mg.
42. The method according to Embodiment 40, wherein the unit dose is about 50 mg.
43. The method according to Embodiment 40, wherein the unit dose is about 100 mg.
44. The method according to Embodiment 40, wherein the unit dose is about 200 mg.
45. The method according to any one of Embodiments 40-44, wherein taladegib is administered once a day.
46. The method according to any one of Embodiments 40-45, wherein taladegib is administered to the subject for at least 4 weeks, at least 8 weeks, at least 12 weeks, at least 16weeks, at least 20 weeks, at least 24 weeks, or longer.
47. The method according to any one of the preceding Embodiments, wherein taladegib is administered as a tablet.
48. The method according to Embodiment 47, wherein the tablet comprises between 5 and 25% of taladegib, between 20 and 50% HPMCAS-H, between 15 and 45% mannitol, between 15and 45% microcrystalline cellulose, between 1 and 5% croscarmellose sodium, between 0.5 and 5% silicon dioxide, between 0.5 and 5% sodium stearyl fumarate, and between 1 and 10% OPADRY®.
49. A method of treating pulmonary fibrosis, the method comprising administering to a subject in need thereof taladegib, or a pharmaceutically acceptable salt thereof, according to a treatment regimen that reduces pulmonary vascular volume.
50. A method of treating pulmonary fibrosis, the method comprising administering to a subject in need thereof taladegib, or a pharmaceutically acceptable salt thereof, wherein pulmonary vascular volume is reduced.
51. A method of reducing pulmonary vascular volume in a subject in need thereof, the method comprising administering to the subject an effective amount of taladegib.
52. The method according to any one of Embodiments 49-51, wherein the reduction in pulmonary vascular volume is measured by a diagnostic method comprising a step of collecting High Resolution Computed Tomography images of the subject.
53. The method of Embodiment 52, wherein the diagnostic method further comprises the use of machine learning methodologies.
54. The method according to any one of Embodiments 49-53, wherein the reduction in pulmonary vascular volume is the change from baseline pulmonary vascular volume of about −0.05 percentage points, about −0.10 percentage points, about −0.15 percentage points, about −0.20 percentage points, about −0.25 percentage points, about −0.30 percentage points, about −0.35 percentage points, about −0.40 percentage points, about −0.45 percentage points, about −0.50 percentage points, about −0.55 percentage points, about −0.60 percentage points, or about −0.65 percentage points.

55. The method according to any one of Embodiments 49-54, wherein the treatment regimen comprises administering a total daily dose of taladegib of about 10-200 mg.
56. The method according to any one of Embodiments 49-54, wherein the treatment regimen comprises administering a total daily dose of taladegib of about 100-200 mg.
57. The method according to any one of Embodiments 49-54, wherein the treatment regimen comprises administering a total daily dose of taladegib of about 200 mg.
58. The method according to any one of Embodiments 49-57, wherein taladegib is administered as one or more unit doses.
59 The method according to Embodiment 58, wherein the unit dose is about 25 mg.
60 The method according to Embodiment 58, wherein the unit dose is about 50 mg.
61. The method according to Embodiment 58, wherein the unit dose is about 100 mg.
62 The method according to Embodiment 58, wherein the unit dose is about 200 mg.
63. The method according to any one of Embodiments 58-62, wherein taladegib is administered once a day.
64. The method according to any one of Embodiments 58-63, wherein taladegib is administered to the subject for at least 4 weeks, at least 8 weeks, at least 12 weeks, at least 16 weeks, at least 20 weeks, at least 24 weeks, or longer.
65. The method according to any one of Embodiments 49-64, wherein taladegib is administered as a tablet.
66. The method according to Embodiment 65, wherein the tablet comprises between 5 and 25% of taladegib, between 20 and 50% HPMCAS-H, between 15 and 45% mannitol, between 15 and 45% microcrystalline cellulose, between 1 and 5% croscarmellose sodium, between 0.5 and 5% silicon dioxide, between 0.5 and 5% sodium stearyl fumarate, and between 1 and 10% OPADRY®.

EXAMPLES

Example 1. A Phase 2A Phase 2, Multi-Center Study Evaluating the Safety and Efficacy of ENV-101 (Taladegib) in Subjects with Idiopathic Pulmonary Fibrosis (IPF)

Study Design. Eligible subjects with mild to moderate IPF were randomized to receive placebo or ENV-101 as a daily oral dose for 12 consecutive weeks of treatment. Following treatment, subjects were observed for an additional 6 weeks. Subjects participated in a Screening Visit, a Day 1 randomization visit, a telephone visit at Week 1, visits at Week 6 and Week 12 during the treatment period and a follow-up visit at Week 18. All subjects were randomized to receive either placebo or 200 mg of taladegib (ENV-101). During the treatment period, if a subject experienced an adverse event that is related to the study medication, the dose of the study drug was permitted to be modified based on the type of adverse event observed and after consultation with the Sponsor and Medical Monitor. A study subject was considered to have completed the study if he or she completed all study visits including the last visit or the last scheduled procedure shown in the Schedule of Activities (SoA).

Study Population. Inclusion Criteria:

1. Males and females greater than 40 years of age.
2. Idiopathic Pulmonary Fibrosis diagnosis based upon American Thoracic Association, Japanese Respiratory Society, European Respiratory Society, Latin American Thoracic Association guidelines within the last 7 years. Diagnosis will be confirmed to be consistent with IPF by centrally read high resolution computed tomography (HRCT) obtained at the Screening Visit or previous HRCT scan performed within 30 days of the Screening Visit may be used.
3. Ability to successfully perform lung function tests.
4. Percent predicted forced vital capacity (FVC) of >50% at the Screening Visit.
5. Percent predicted diffusion capacity of the lungs for carbon monoxide ($DL_{CO}$)≥35%, adjusted for hemoglobin (Hgb) at the Screening Visit.
6. Resting $O_2$ saturation of >90%, obtained on room air at the Screening Visit.
7. Life expectancy of >12 months, as per the clinical judgement of the Investigator.
8. Subjects are willing to remain on study treatment for the duration of the study.
9. Subjects have a full understanding of the informed consent.

Exclusion Criteria:

1. Evidence of other known causes of interstitial lung disease (ILD) (e.g., domestic and occupational environmental exposures, connective-tissue disease [CTD], and drug toxicity), lung transplant expected within 12 months of screening or evidence of clinically significant lung disease other than IPF including but not limited to asthma, chronic obstructive pulmonary disease (COPD), uncontrolled pulmonary hypertension and emphysema where computed tomography (CT)-assessed extent of emphysema is greater than extent of fibrosis.
2. Forced expiratory volume in one second (FEV1)/FVC ratio <0.7 at Screening.
3. Acute exacerbation of IPF, in the opinion of the Investigator, within 30 days prior to Day 1.
4. History of malignancy, including carcinoma during the preceding 5 years. With the following exceptions:
   a. Prior history of in situ basal or squamous cell skin cancer that was successfully treated with curative therapies.
   b. Subjects with other malignancies if they have been continuously disease free for at least 5 years prior to the Screening Visit.
   c. Subjects with prostate cancer that are managed by surveillance are also eligible.
5. Current use of supplemental oxygen for any condition unless prior approval was received from the Sponsor.
6. Smoking within 6 months of the Screening Visit, current smoker, or unwillingness to refrain from smoking during the clinical trial duration. Subjects with a positive cotinine test at screening will be excluded.
7. Presence of active infection on Day 1 or confirmed active human immunodeficiency virus (HIV), Hepatitis B virus (HBV) or Hepatitis C virus (HCV).
8. Occurrence of serious illness requiring hospitalization within 90 days prior to Day 1.
9. Current or previous use (within 30 days prior to Day 1) of the following:
   a. N-acetylcysteine
   b. endothelin receptor antagonist
   c. riociguat
   d. prostacyclin or prostacyclin analogue
   e. Warfarin for IPF f. Cytotoxic agents (e.g., colchicine if used for IPF)
g. Radiation to the lungs
h. Pulmonary rehabilitation
i. Investigational agent for IPF
j. Immunosuppressive medications (e.g. methotrexate, azathioprine)
k. Systemic or inhaled glucocorticosteroids
l. Antifibrotic therapy (e.g., nintedanib, pirfenidone)

10. Regular use of phosphodiesterase type-5 inhibitor, occasional use for erectile dysfunction will be allowed.
11. Use of drugs that are known moderate or stronger CYP3A4 inhibitors or inducers within 12 days prior to Day 1.
12. Any condition, including significant laboratory findings, prior or current history of alcohol or drug abuse, or inability to swallow medication tablets, that in the opinion of the Investigator, constitutes a risk or contraindication for participation in the study.
13. Males and females of reproductive potential who are sexually active and unwilling to use birth control for the duration of the study and for 3 months after their final dose.
14. Females that are pregnant or nursing.
15. Females and males that are unwilling to refrain from blood or blood product donation for the duration of the study and for 30 days after their final study dose.
16. Males who are unwilling to refrain from sperm donation and females who are unwilling to refrain from egg donation for the duration of the study and for 3 months after their final study dose.
17. Subjects with a history of a severe allergic reaction or anaphylactic reaction or known hypersensitivity to any component of ENV-101.
18. Subjects who are immediate family members (spouse, parent, child, or sibling; biological or legally adopted) of personnel directly affiliated with the study investigative site or the study Sponsor.

The study objectives and endpoints are set forth in Table 1:

TABLE 1

| Objectives | Endpoints |
|---|---|
| **Primary** | |
| To evaluate the safety of ENV-101 when compared to placebo in subjects with IPF. | Safety was assessed by the incidence and severity of clinical laboratory abnormalities, change from baseline in vital sign measurements, oxygen saturation, frequency and severity of adverse events and number of hospitalizations for the duration of the study. |
| **Secondary** | |
| To evaluate the effect of ENV-101 as measured by lung function.<br>To evaluate the effect of ENV-101 as measured by patient reported outcome. | Efficacy was assessed by change from baseline of FVC measured in mL at Week 12.<br>Efficacy was assessed by changes from baseline in DLCO at Week 12.<br>Efficacy was assessed by change from baseline of patient reported outcomes by the University of California, San Diego (UCSD) Shortness of Breath Questionnaire (SOBQ) at Week 12. |
| **Exploratory** | |
| To evaluate the effects of ENV-101 as measured by High Resolution Computed Tomography (HRCT).<br>To evaluate the effects of ENV-101 as measured by lung function and patient reported outcome changes over time.<br>To estimate the extent to which changes from baseline in UCSD SOBQ are concordant with changes in FVC over time. | Efficacy was assessed by change from baseline of HRCT by quantitative measurements such as volume and texture and qualitative measurements such as fibrosis, ground glass, honeycombing and bronchiectasis at Week 12.<br>Efficacy was assessed by changes from baseline in FVC, DLco, and UCSD SOBQ over time. |

The study medication was supplied as single dose beige-colored or aquamarine-colored tablets, containing either 100 mg taladegib per tablet or 0 mg taladegib per tablet (i.e., placebo).

The dosing regimen evaluated in this study was ENV-101 or placebo administered daily. The dose of ENV-101 studied was 200 mg. Subjects randomized to ENV-101 took two 100 mg tablets daily for the 200 mg dose, while subjects randomized to placebo took two placebo tablets daily. Subjects took both tablets at the same time, and it was recommended that subjects take the dose at the same time each day, ideally in the morning prior to eating. If a subject experienced nausea or other gastrointestinal symptoms, it was recommended that the subject take the dose with a low-fat meal or prior to bedtime.

If a subject experienced an adverse event related to the study medication, the Investigator, in consultation with the study Sponsor and Medical Monitor, could elect to reduce the subject's dose. The dose could be reduced to a minimum of 100 mg. Similarly, if a subject missed >3 consecutive days of study medication dosing due to tolerability, it was recommended that the subject contact the PI and the PI and Medical Monitor discuss the case management of the subject.

Results. The subject demographics at the beginning of the study (i.e., baseline) are set forth in Table 2.

TABLE 2

| Characteristic | ENV-101 (n = 21) | Placebo (n = 20) |
|---|---|---|
| Age (years, mean) | 69.7 ± 9.0 | 71.2 ± 5.5 |

TABLE 2-continued

| Characteristic | ENV-101 (n = 21) | Placebo (n = 20) |
|---|---|---|
| Male | 86% | 80% |
| BMI (kg/$m^2$, mean ± SD) | 26.3 ± 3.4 | 26.5 ± 3.3 |
| Baseline FVC (mL, mean ± SD) | 2658 ± 742 (n = 20) | 2778 ± 624 |
| Baseline ppFVC (mean ± SD) | 81 ± 20 | 85 ± 17 |
| Baseline $DL_{co}$ (mL/min/mmHg) | 22.1 ± 2.5 (n = 18) | 22.6 ± 2.6 (n = 18) |
| Time since IPF diagnosis (years) | 1.2 | 1.5 |
| Baseline UCSD SOBQ (mean ± SD) | 43 ± 25 | 22 ± 19 |

5/7 patients had discontinued pirfenidone prior to study entry due to adverse events. No subjects reported prior use of nintedanib.

At 6 weeks, subjects who had been administered 200 mg taladegib once a day demonstrated an average increase from baseline in forced vital capacity (FVC) of about 48.8 mL, as compared to subjects administered placebo, who demonstrated an average decrease from baseline in forced vital capacity (FVC) of about −7.4 mL. At 12 weeks, the disparity between treated subjects and those administered is more pronounced, with treated subjects experiencing an average increase from baseline of forced vial capacity (FVC) of about 60.0 mL. Subjects in the placebo arm experienced an average decrease from baseline in forced vital capacity (FVC) of about −46.8 mL. Such disparity was statistically significant and demonstrates that taladegib improves lung function as compared to untreated subjects who show a continued decline in lung function. See FIG. 1A. Notably, all subjects in the study experienced significant decline in FVC in the observation period (i.e., weeks 12-18).

Figure 1A:
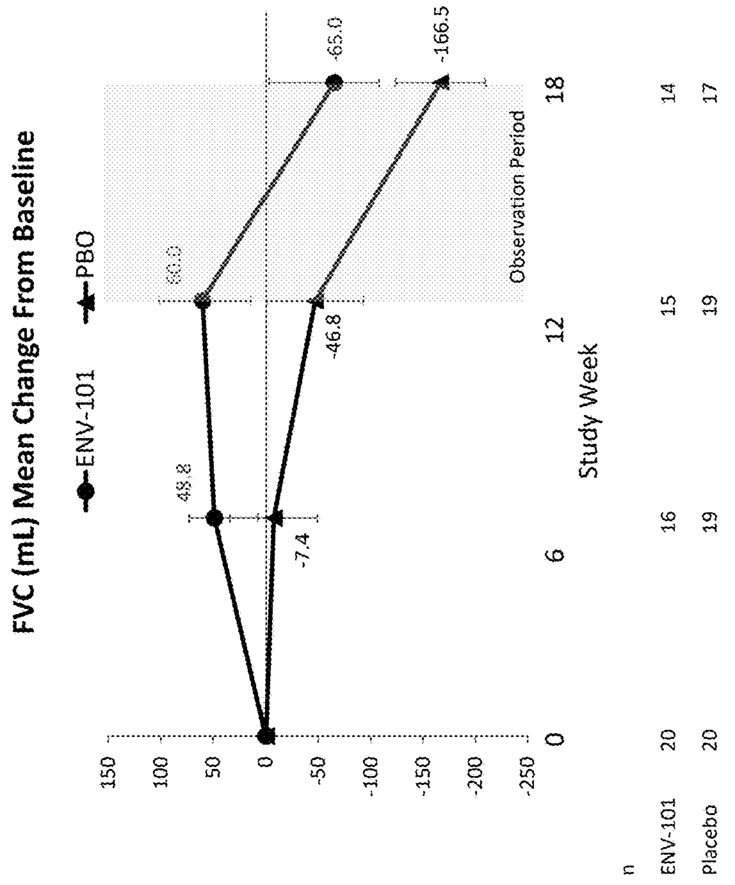
FIG. 1A is a graph that shows the mean change from baseline of FVC (mL) in IPF subjects treated with 200 mg QD taladegib (also known as ENV-101) (●) as compared to the placebo group (▲). At 6 weeks, the mean FVC (mL) for the treated group (n=16) was 48.8, as compared to the mean FVC (mL) for the placebo group (n=19) of −7.4. At 12 weeks, the mean FVC (mL) for the treated group (n=15) was 60.0, as compared to the mean FVC (mL) for the placebo group (n=19) of −46.8 (p=0.07).

Similarly, the ppFVC change from baseline in treated and untreated subjects is shown in FIG. 1B. Subjects treated with 200 mg taladegib once a day for 12 weeks experienced an average change from baseline in ppFVC of about 1.9%, as compared to placebo subjects who demonstrated an average change from baseline in ppFVC of about −1.3%. Notably, all subjects in the study experienced significant decline in ppFVC in the observation period (i.e., weeks 12-18).

Figure 2:
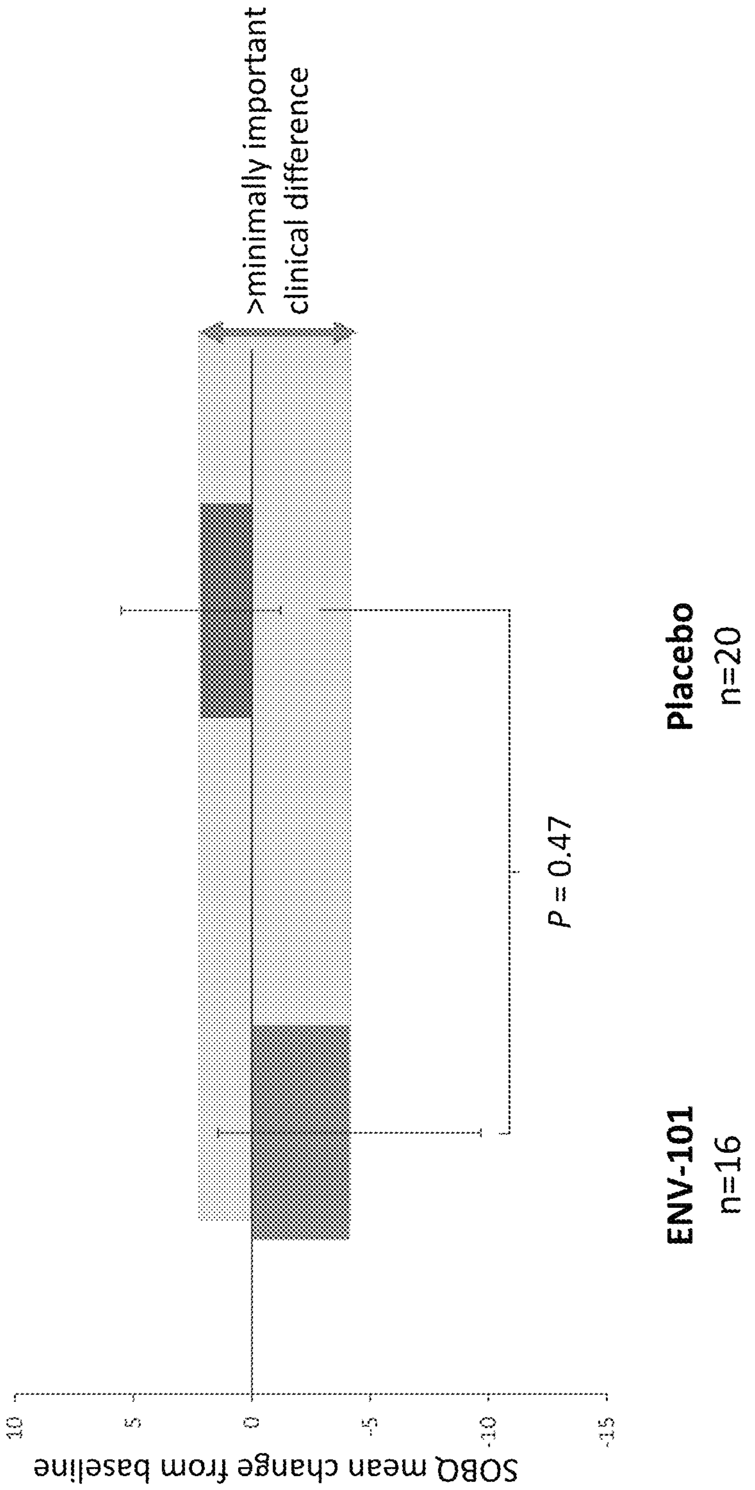
FIG. 2 is a bar graph that depicts the mean change from baseline of study subjects' responses to the UCSD Shortness of Breath Questionnaire (SOBQ). Subjects treated with 200 mg taladegib once a day reported improvement in how they feel on the SOBQ, as compared with subjects in the placebo arm who reported a decline on the SOBQ. Although the results are not statistically significant, they represent a qualitative improvement in patient-reported outcomes.

Subjects administered 200 mg taladegib once a day also reported improvement in how they feel on the UCSD Shortness of Breath Questionnaire, as demonstrated by FIG. 2. Although the results are not statistically significant, they represent a qualitative improvement in patient-reported outcomes.

Figure 3:
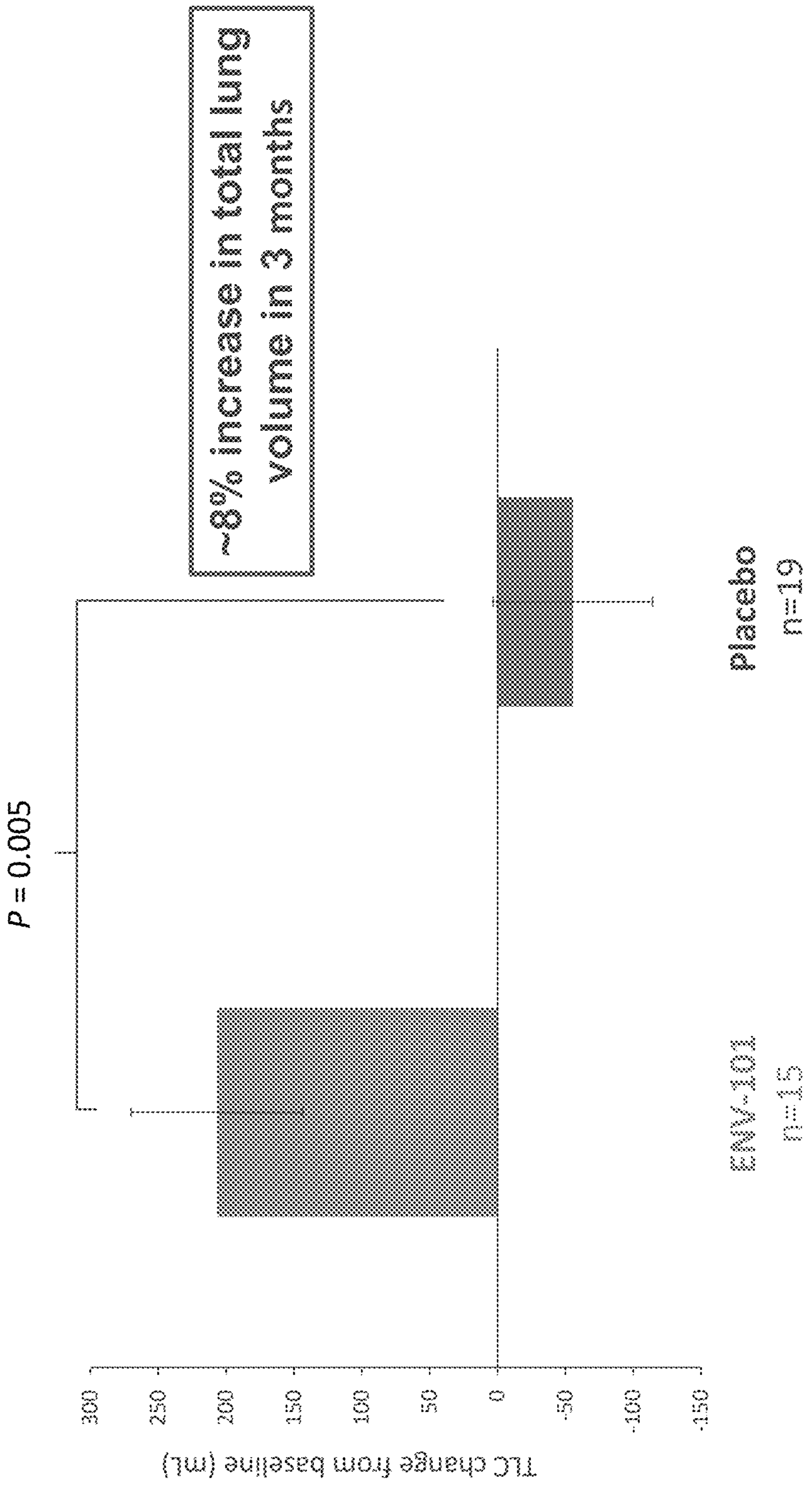
FIG. 3 is a bar graph that depicts the quantitative assessment of total lung capacity (TLC) in subjects treated with 200 mg taladegib once a day. Subjects treated with taladegib experienced an increase in total lung capacity (TLC) of about 200 mL, as compared to subjects in the placebo arm that experienced a decrease in total lung capacity (TLC) of about 56 mL over the same period. The increase in total lung capacity experienced in the treated arm was statistically significant (p-0.005) and represented about 8% increase in total lung capacity over the three month treatment period.

FIG. 3 is a bar graph that demonstrates the quantitative assessment of total lung capacity (TLC) in subjects treated with 200 mg taladegib once a day for 12 weeks. As shown in FIG. 3, subjects treated with taladegib experienced an increase in total lung capacity (TLC) of about 200 mL, as compared to subjects in the placebo arm that experienced a decrease in total lung capacity over the same period. The increase in total lung capacity experienced in the treated arm was statistically significant and represented about 8% increase in total lung capacity over the three month treatment period.

Figure 4:
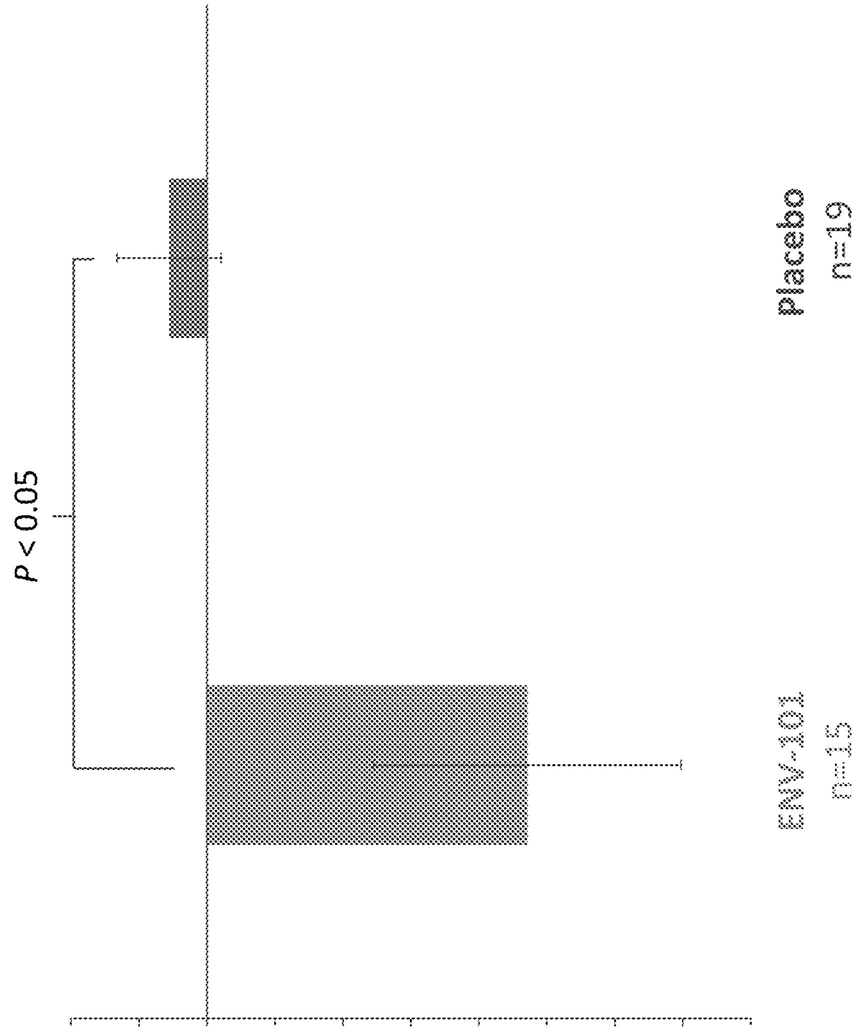
FIG. 4 is a bar graph that depicts the quantitative measure of change from baseline in percent quantitative interstitial lung disease (% QILD). Subjects in the treatment arm experienced a change in % QILD of about −9%, whereas subjects in the placebo arm experienced a change from baseline of % QILD of about 1.1%. Such results were statistically significant.
Figure 5:
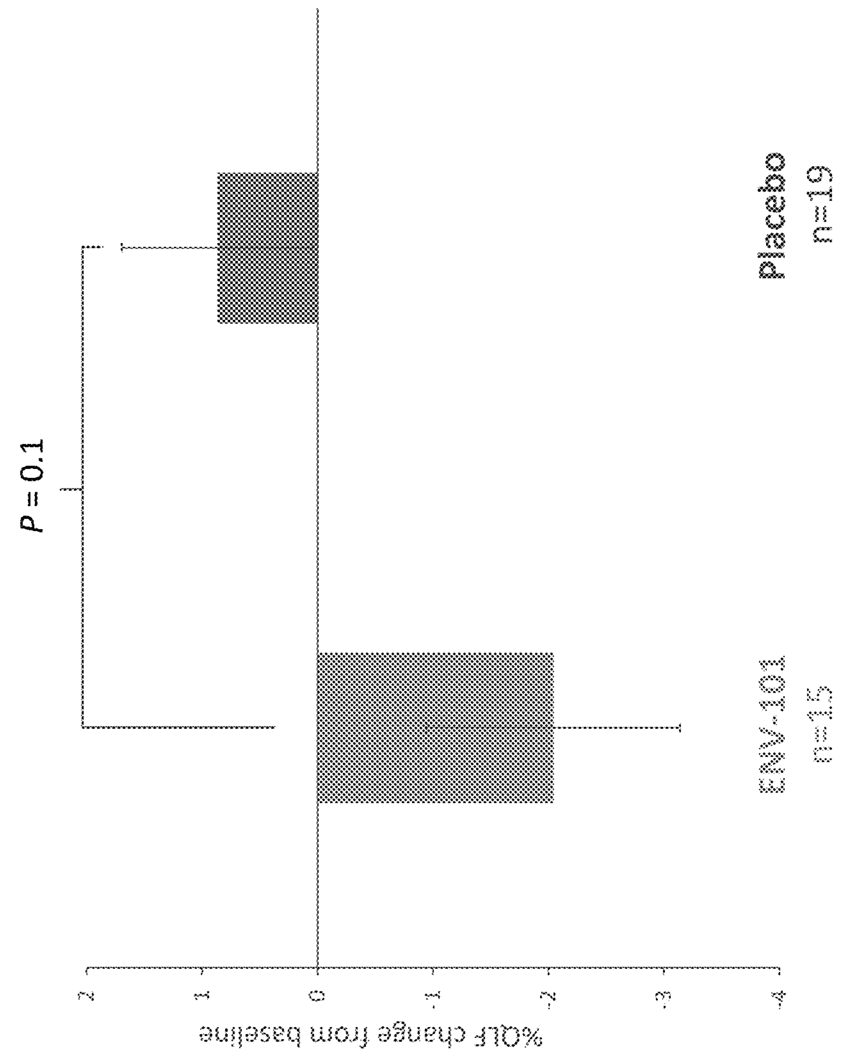
FIG. 5 is a bar graph that depicts the quantitative measure of change from baseline in percent quantitative lung fibrosis (% QLF). Subjects in the treatment arm experienced a change in % QLF of about −2%, whereas subjects in the placebo arm experienced a change from baseline of % QLF of about 0.9%.
Figure 6:
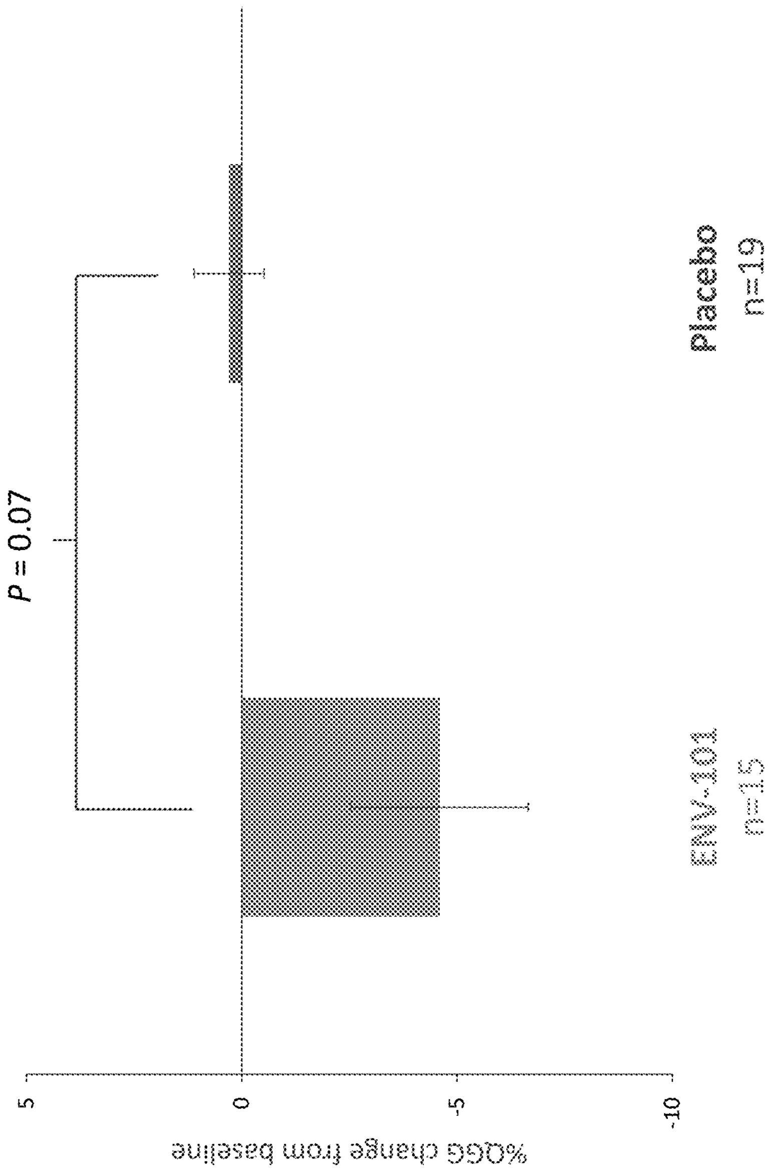
FIG. 6 is a bar graph that depicts the quantitative measure of change from baseline in % quantitative ground glass opacity (% QGG). Subjects in the treatment arm experienced a change in % QGG of about −4.6%, whereas subjects in the placebo arm experienced a change from baseline of % QGG of about 0.3%.

FIG. 4-6 are bar graphs that demonstrate the quantitative decreases in measures of lung fibrosis. Such decreases in lung fibrosis demonstrate a reversal of fibrosis after 12 weeks of treatment with 200 mg taladegib once a day for 12 weeks. FIG. 4 is a quantitative measure of change from baseline in percent quantitative interstitial lung disease (% QILD). Subjects in the treatment arm experienced a change in % QILD of about −9%, whereas subjects in the placebo arm experienced a change from baseline of % QILD of about 1.1%. Such results were statistically significant.

FIG. 5 is a quantitative measure of change from baseline in percent quantitative lung fibrosis (% QLF). Subjects in the treatment arm experienced a change in % QLF of about −2%, whereas subjects in the placebo arm experienced a change from baseline of % QLF of about 0.9%.

FIG. 6 is a quantitative measure of change from baseline in percent quantitative ground glass opacity (% QGG). Subjects in the treatment arm experienced a change in % QGG of about −4.6%, whereas subjects in the placebo arm experienced a change from baseline of % QGG of about 0.3%.

Figure 7:
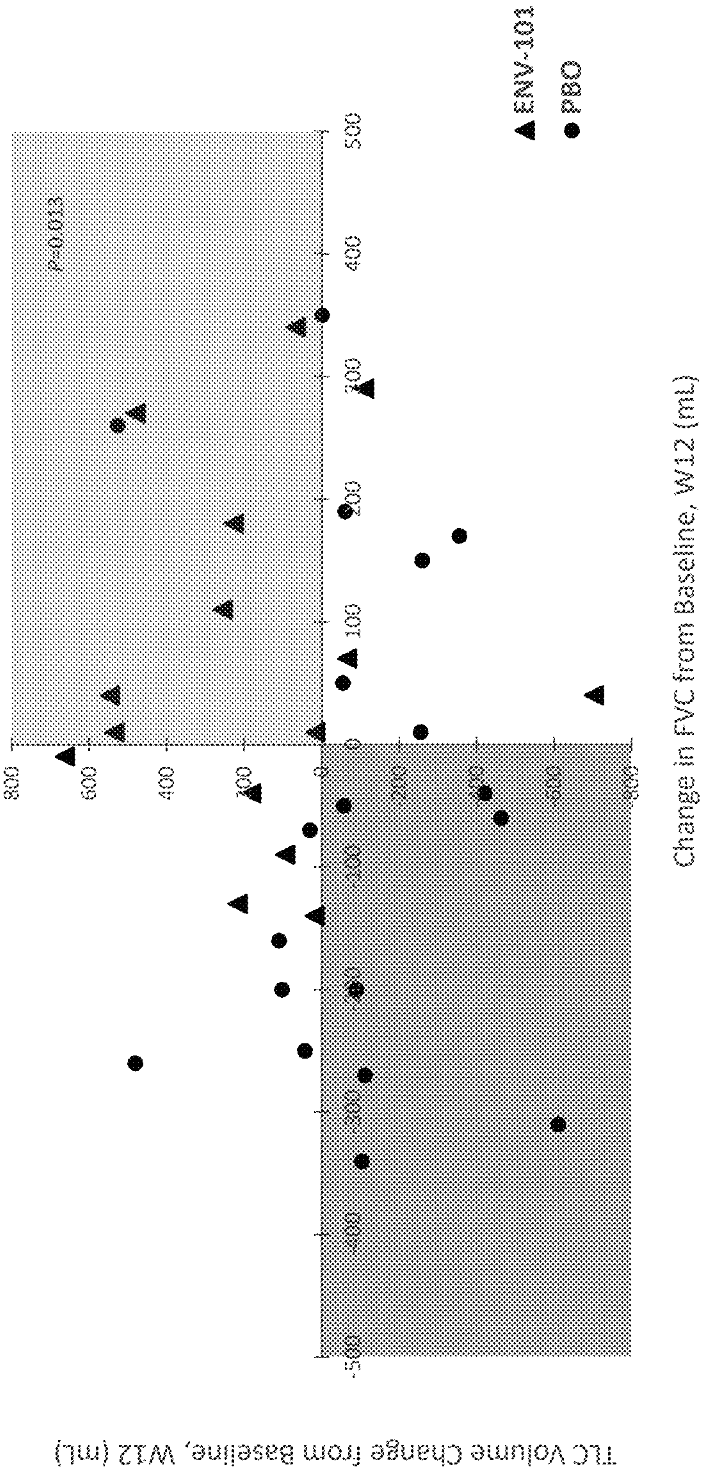
FIG. 7 is a scatter plot that demonstrates the increase in total lung capacity correlates with increased FVC after 12 weeks of treatment with taladegib. A significant number of subjects treated with taladegib experienced an increase in total lung capacity and an increase in forced vital capacity.

FIG. 7 is a scatter plot that demonstrates the increase in total lung capacity correlates with increased FVC after 12 weeks of treatment with taladegib. A significant number of subjects treated with taladegib (▲) experienced an increase in total lung capacity and an increase in forced vital capacity.

A post-hoc analysis utilizing deep learning models developed by Qureight (using machine learning methodologies such as 3D convolutional neural networks), were employed to quantify lung volume (Lung8), vessel volume (Vascul8), fibrosis extent (Fibr8) and airway volume (Air8) from High Resolution Computed Tomography images. Deep learning-based CT biomarkers provide an alternate, non-invasive way to predict disease progression and/or assess treatment effects in antifibrotic clinical trials.

34 patients with baseline and week 12 HRCTs were available for model analysis. Of the 34 patients, 18 patients received placebo, and 16 received ENV-101. Group comparisons were performed with an independent t-test, and linear regression assessed variable relationships. Effect sizes were calculated using Hedges' G to account for sample size bias. A p-value<0.05 was considered significant.

Figure 8:
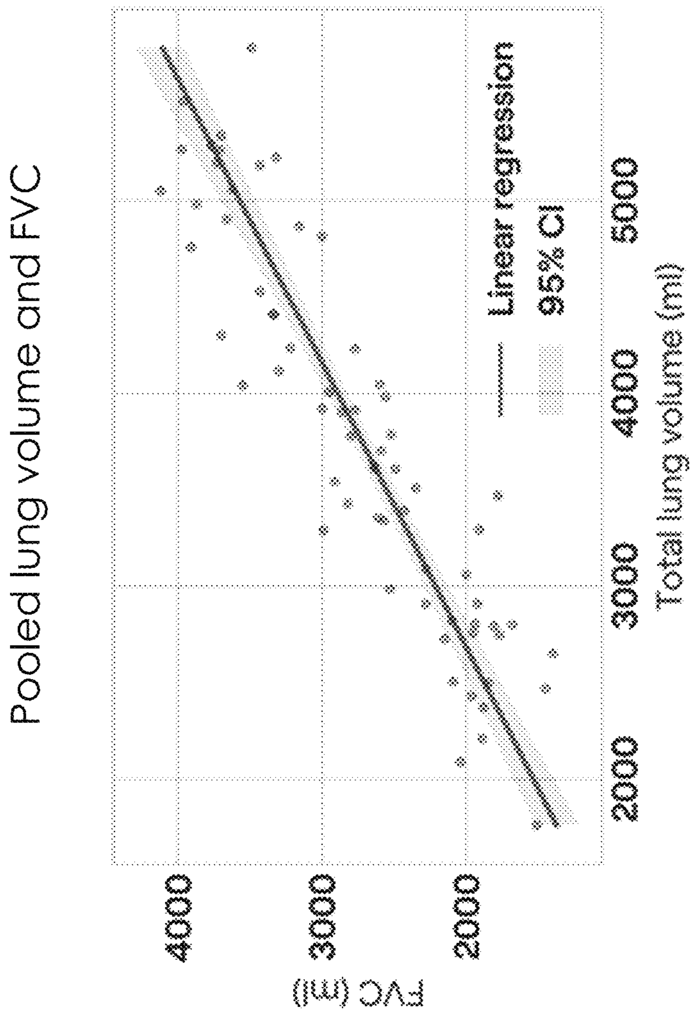
FIG. 8 shows a plot of Lung8 lung volume against forced vital capacity (FVC) for measurements pooled across time points.

FIG. 8 demonstrates a strong correlation between lung volume and absolute forced vital capacity FVC ($r^2$=0.83, p<0.0001). Percent extent of fibrosis, normalised to lung volume, inversely correlated with percent predicted FVC ($r^2$=0.52, p<0.0001).

Figure 9:
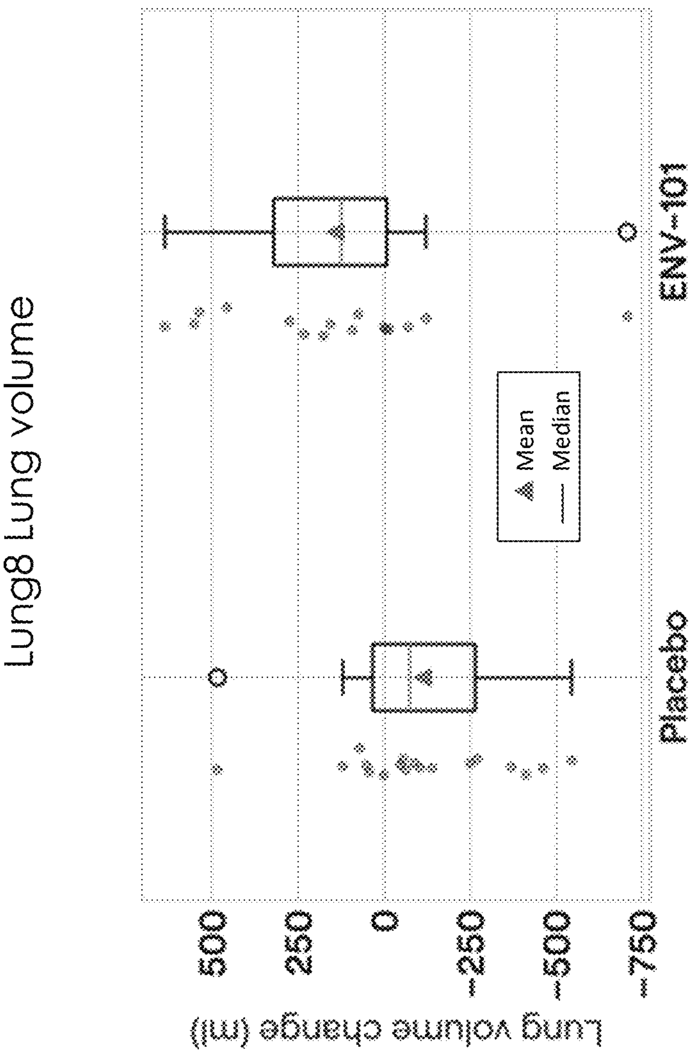
FIG. 9 shows a comparison of the change in lung volume, between placebo and ENV-101 arms, at week 12.
Figure 10:
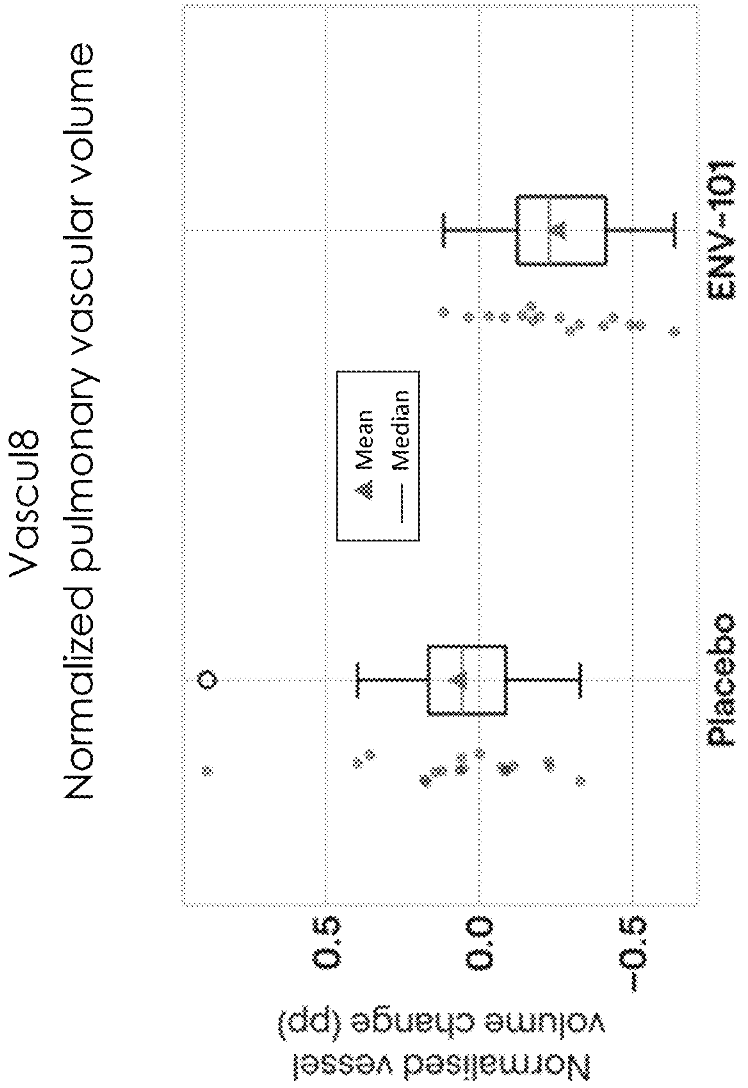
FIG. 10 shows a comparison of the change in pulmonary vascular volume (normalized to lung volume), between placebo and ENV-101 arms, at week 12.
Figure 11:
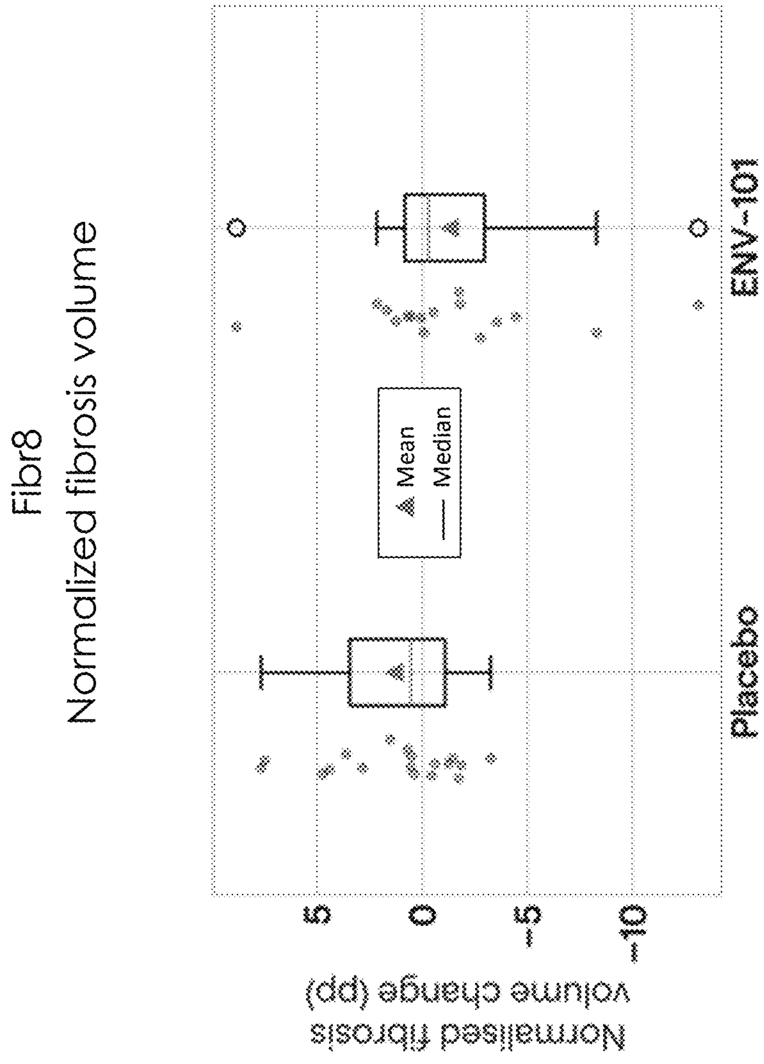
FIG. 11 shows a comparison of the change in fibrosis extent (normalized to lung volume), between placebo and ENV-101 arms, at week 12.

Compared to placebo, patients receiving ENV-101 demonstrated:

- a significant improvement in % predicted FVC (p—0.03, effect size—0.78);
- a significant increase in total lung volume, see FIG. 9 (PBO: −113.7ml vs ENV: 142.28ml, p—0.014, effect size—0.87) ;
- a significant reduction in normalised pulmonary vascular volume, see FIG. 10 (PBO: 0.07% vs ENV: −0.25%, p=0.0007, effect size=−1.28); and
- reduced lung fibrosis, see FIG. 11 (PBO: 1.32% vs ENV: −1.32%, p=0.063, effect size=−0.64).

| Week 12 | PBO | ENV-101 | p | effect size |
|---|---|---|---|---|
| Lung volume change | −113.07 ml | 142.28 ml | 0.014 | 0.87 |
| Change in Pulmonary vascular volume | 0.07% | −0.25% | 0.0007 | −1.28 |
| Change in Fibrosis | 1.32% | −1.32% | 0.063 | 0.64 |

In conclusion, patients treated with ENV-101 over 12 weeks showed significantly improved lung volume, significantly reduced pulmonary vascular volume and reduced fibrosis.

The invention claimed is:

1. A method of reversing pulmonary fibrosis, the method comprising administering taladegib, or a pharmaceutically acceptable salt thereof, to a subject suffering from or diagnosed with pulmonary fibrosis according to a treatment regimen that improves lung function in the subject, wherein the improvement in lung function comprises one or more of the following:
an increase in total lung capacity (TLC) as compared to baseline TLC;
a reduction in one or more measures of lung fibrosis;
an increase in lung volume; or
reducing pulmonary vascular volume.

2. The method according to claim 1, wherein the improvement in lung function is continuous improvement during the period in which the subject is administered taladegib.

3. The method according to claim 1, wherein the improvement in lung function is maintained or persists after the period in which the subject was administered taladegib.

4. The method according to claim 1, wherein the improvement in lung function comprises an increase in total lung capacity (TLC) as compared to baseline TLC.

5. The method according to claim 4, wherein TLC is measured by high resolution computed tomography (HRCT).

6. The method according to claim 4, wherein TLC is increased by about 5%, about 6%, about 7%, about 8%, about 9%, about 10%, about 11%, about 12%, about 13%, about 14%, or about 15% from baseline.

7. The method according to claim 4, wherein TLC is increased by at least 5%, at least 6%, at least 7%, at least 8%, at least 9%, at least 10%, at least 11%, at least 12%, at least 13%, at least 14%, or at least 15% from baseline.

8. The method according to claim 4, wherein TLC is increased by about 50 mL, about 75 mL, about 100 mL, about 125 mL, about 150 mL, about 175 mL, about 200 mL, about 225 mL, about 250 mL, about 275 mL, or about 300 mL from baseline.

9. The method according to claim 4, wherein TLC is increased by at least 50 mL, at least 75 mL, at least 100 mL, at least 125 mL, at least 150 mL, at least 175 mL, at least 200 mL, at least 225 mL, at least 250 mL, at least 275 mL, or at least 300 mL from baseline.

10. The method according to claim 1, wherein the improvement in lung function comprises a reduction in one or more measures of lung fibrosis.

11. The method according to claim 10, wherein the reduction in one or more measures of lung fibrosis is selected from percent quantitative lung fibrosis (% QLF), percent ground glass opacity (% QGG), or percent honeycombing.

12. The method according to claim 11, wherein the percent quantitative lung fibrosis (% QLF) is a change from baseline % QLF of about −0.5%, about −0.6%, about −0.7%, about −0.8%, about −0.9%, about −1.0%, about β1.1%, about −1.2%, about β1.3%, about −1.4%, about −1.5%, about −1.6%, about −1.7%, about −1.8%, about −1.9%, about −2.0%, about −2.1%, about −2.2%, about −2.3%, about −2.4%, about −2.5%, about −2.6%, about −2.7%, about −2.8%, about −2.9%, or about −3.0%.

13. The method according to claim 11, wherein the percent quantitative lung fibrosis (% QLF) is a change from baseline % QLF of at least −0.5%, at least −0.6%, at least −0.7%, at least −0.8%, at least −0.9%, at least −1.0%, at least −1.1%, at least −1.2%, at least −1.3%, at least −1.4%, at least −1.5%, at least −1.6%, at least −1.7%, at least −1.8%, at least −1.9%, at least −2.0%, at least −2.1%, at least −2.2%, at least −2.3%, at least −2.4%, at least −2.5%, at least −2.6%, at least −2.7%, at least −2.8%, at least −2.9%, or at least −3.0%.

14. The method according to claim 11, wherein the percent ground glass opacity (% QGG) is a change from baseline % QGG of about −0.5%, about −1.0%, about −1.5%, about −2.0%, about −2.5%, about −3.0%, about −3.5%, about −4.0%, about −4.5%, about −5.0%, about −5.5%, about −6.0%, about −6.5%, about −7.0%, about −7.5%, about −8.0%, about −8.5%, about −9.0%, about −9.5%, or about −10.0%.

15. The method according to claim 11, wherein the percent ground glass opacity (% QGG) is a change from baseline % QGG of at least −0.5%, at least −1.0%, at least −1.5%, at least −2.0%, at least −2.5%, at least −3.0%, at least −3.5%, at least −4.0%, at least −4.5%, at least −5.0%, at least −5.5%, at least −6.0%, at least −6.5%, at least −7.0%, at least −7.5%, at least −8.0%, at least −8.5%, at least −9.0%, at least −9.5%, or at least −10.0%.

16. The method according to claim 1, wherein the improvement in lung function comprises an increase in lung volume.

17. The method according to claim 1, wherein the pulmonary fibrosis is idiopathic pulmonary fibrosis (IPF) or non-IPF progressive pulmonary fibrosis (PPF).

18. The method according to claim 1, wherein the treatment regimen comprises administering a total daily dose of taladegib of about 10-200 mg.

19. The method according to claim 1, wherein the treatment regimen comprises administering a total daily dose of taladegib of about 100-200 mg.

20. The method according to claim 1, wherein the treatment regimen comprises administering a total daily dose of taladegib of about 200 mg.

21. The method according to claim 1, wherein taladegib is administered as one or more unit doses.

22. The method according to claim 21, wherein the unit dose is about 25 mg.

23. The method according to claim 21, wherein the unit dose is about 50 mg.

24. The method according to claim 21, wherein the unit dose is about 100 mg.

25. The method according to claim 21, wherein the unit dose is about 200 mg.

26. The method according to claim 21, wherein taladegib is administered once a day.

27. The method according to claim 21, wherein taladegib is administered to the subject for at least 4 weeks, at least 8 weeks, at least 12 weeks, at least 16 weeks, at least 20 weeks, at least 24 weeks, or longer.

28. The method according to claim 1, wherein taladegib is administered as a tablet.

29. The method according to claim 28, wherein the tablet comprises in percentage weight between 5 and 25% of taladegib, between 20 and 50% hydroxypropylmethylcellulose acetate succinate (HPMCAS-H), between 15 and 45% mannitol, between 15 and 45% microcrystalline cellulose, between 1 and 5% croscarmellose sodium, between 0.5 and 5% silicon dioxide, between 0.5 and 5% sodium stearyl fumarate, and between 1 and 10% film coating.

* * * * *